(12) United States Patent  
Spaid

(10) Patent No.: US 7,101,467 B2  
(45) Date of Patent: Sep. 5, 2006

(54) MIXED MODE MICROFLUIDIC SYSTEMS

(75) Inventor: Michael A. Spaid, Mountain View, CA (US)

(73) Assignee: Caliper Life Sciences, Inc., Mountain View, CA (US)

( * ) Notice: Subject to any disclaimer, the term of this patent is extended or adjusted under 35 U.S.C. 154(b) by 444 days.

(21) Appl. No.: 10/744,915

(22) Filed: Dec. 22, 2003

(65) Prior Publication Data

US 2004/0188254 A1    Sep. 30, 2004

Related U.S. Application Data

(63) Continuation-in-part of application No. 10/386,900, filed on Mar. 4, 2003.

(60) Provisional application No. 60/381,306, filed on May 17, 2002, provisional application No. 60/361,957, filed on Mar. 5, 2002.

(51) Int. Cl.  
*G01N 27/447* (2006.01)

(52) U.S. Cl. ........................ 204/453; 204/451

(58) Field of Classification Search ............... 422/99, 422/100; 204/450–455, 600–604  
See application file for complete search history.

(56) References Cited

U.S. PATENT DOCUMENTS 5,726,404 A    3/1998    Brody et al.

6,695,009 B1 *    2/2004    Chien et al. ............... 137/827  
2003/0230486 A1    12/2003    Chien et al.

FOREIGN PATENT DOCUMENTS

WO    WO-02/10732 A1    2/2002  
WO    WO-03/006133 A2    1/2003

* cited by examiner

*Primary Examiner*—Alex Noguerola  
(74) *Attorney, Agent, or Firm*—Donald R. McKenna; Ann C. Petersen

(57) ABSTRACT

Methods and systems that employ hybrid fluid flow profiles for optimized movement of materials through channel networks. These systems employ hybrid pressure-based and electrokinetic based flow systems for moving materials through interconnected channel networks while maintaining interconnection among the various channel segments. In particular, the invention is generally directed to channel networks where flow in a first channel segment is driven by pressure flow with its consequent parabolic flow profile, while flow in an interconnected channel segment is dominated by electrokinetic flow with its consequent plug flow profile. The invention also provides channel networks wherein fluid flow in channel segments is driven by both pressure and electric field and the multiple species contained in a fluid plug are separated (and can be concentrated) by altering the applied pressure and electric fields in the various channel segments of the channel networks.

19 Claims, 18 Drawing Sheets

MIXED MODE MICROFLUIDIC SYSTEMS

CROSS-REFERENCE TO RELATED APPLICATION

This application is a continuation-in-part of pending U.S. application Ser. No. 10/386,900 filed Mar. 4, 2003, which claims the benefit of U.S. Provisional Application Nos. 60/361,957 filed Mar. 5, 2002 and 60/381,306 filed May 17, 2002, each of which is incorporated herein be reference in their entirety for all purposes.

BACKGROUND OF THE INVENTION

Microfluidic technology has been heralded as the next technological evolution in biological and chemical research, with its promise of faster, more accurate, readily automatable miniaturized experimentation. Many of the advantages of microfluidic experimentation are evident in the marketplace. For example, the Agilent 2100 Bioanalyzer and its menu of microfluidic devices and reagent kits, supplied by Caliper Technologies Corp., provide a versatile experimentation platform for performing a large number of different analyses important to life science researchers. The data produced by these systems is obtained rabidly in a digitized, highly reproducible fashion.

High throughput experimentation has also been addressed by microfluidic products. The Caliper 250 High Throughput Screening System screens large numbers of different samples, e.g., pharmaceutical test compounds, in a continuous flow microfluidic assay format, to identify potential therapeutic agents from those test compounds. Such systems have the capacity to perform thousands and tens of thousands of assays per day on a single microfluidic device, increasing the throughput of the process while decreasing the footprint and volume of reagents used as compared to conventional screening systems.

While microfluidic systems have been delivering on their promises, the interconnected nature of microfluidic channel networks in the developed systems has led to some limitations of the operability of those systems. By way of example, initial microfluidic systems employed completely electrokinetically driven flow systems. These systems provided precision controllability of fluid and other material movement in all of the interconnected channels of the device, all while moving materials with a flat plug flow profile, with diffusion limited dispersion. However, the use of electric fields to drive material movement also drove electrophoretic separation or biasing of differentially charged species within the channels of the device, yielding data that required more complex data deconvolution. Further, such electrokinetic flow systems also provided slower movement of materials that could reduce throughput where long channel distances were to be traversed. The use of pressure based flow in microfluidic systems results in non-biased movement of differentially charged materials, but creates more highly dispersed flow profiles, resulting from increased Taylor-Aris dispersion in systems that have parabolic flow.

It would generally be desirable to provide microfluidic systems that are optimized to take advantage of the positive aspects of each type of flow profile while eliminating or minimizing the less attractive features of each profile. The present invention meets these and a variety of other needs.

SUMMARY OF THE INVENTION

The present invention generally provides methods and systems that employ hybrid fluid flow profiles for optimized movement of materials through channel networks. These systems employ hybrid pressure-based and electrokinetic based flow systems for moving materials through interconnected channel networks while maintaining interconnection among the various channel segments. In particular, the invention is generally directed to channel networks where flow in a first channel segment is driven by pressure flow with its consequent parabolic flow profile. In an interconnected channel segment, the flow of material is driven electrokinetically which yields its consequent plug flow profile. The methods and systems typically employ an access or tapping channel at the junction of the channels having the different flow profiles to tap-off pressure flow and substitute electrophoretic flow through the junction. This ensures a passing off of flowing material from the first to the second channel segment while changing the flow profile under which that material is moving.

The devices of the present invention are also useful for separating differently charged species from a sample mixture by managing the flow profiles of the various species by controlling the applied pressure or electric field, or alternatively by controlling both the applied pressure as well as the electrical field. Using a fluid control system with multiple pressure and voltage sources, the pressure and/or voltage in any given channel segment of the device can be controlled such that the hydrodynamic flow and electric field in any section of the microfluidic channel network can be set to desired values. The present invention provides devices wherein the fluid flow in different segments of the channel network is independently controlled by overlapping the two different flow profiles, i.e., pressure based and electrokinetically driven, and simultaneously controlling the flow velocity under each of the flow profiles to achieve a net velocity for a given species contained in the fluid to an amount sufficient to facilitate separation and isolation of the differently charged species contained in the fluid-borne sample. Thus, mixtures of two or more sample species (e.g., a neutral substrate and a negatively charged product of an enzymatic reaction) having different electrophoretic mobilities sent into a channel intersection, such as a T-intersection as described below, can be separated completely into separated components in separate channels of the intersection based on the different electrophoretic mobilities of the sample species.

Other novel techniques, similar to selective ion extraction described above, are also described herein for separating and extracting analytes having different mobilities (e.g., different charge and/or mass), in which the microfluidic channel network is configured and dimensioned in such a way to proportion the fluidic driving forces to separate differently charged species in a fluidic sample by utilizing a reduced number of external pressure and voltage sources, e.g., by reducing the number of fluidic reservoirs needed for fluidic control to perform the separation as compared to previously described embodiments. In this way, excess hardware needed for fluid transport can be minimized and the microfluidic device can be operated with fewer fluidic reservoirs compared to previously described designs.

DETAILED DESCRIPTION OF THE INVENTION

I. General

In general, the present invention provides methods and systems for moving of materials in microfluidic channel systems that involve predominantly non-electrokinetic pressure driven flow in one channel segment while involving electrokinetically driven flow in a connected second channel segment. By providing different types of flow profiles in different sections of a microfluidic channel network, one can optimize each segment based upon the needs of the overall operation while minimizing adverse effects that might result from a particular type of flow profile.

As used herein, the phrase "non-electrokinetic pressure flow" refers to flow that is driven by a pressure source external to the channel segment through which such flow is driven, as contrasted to flow that is generated through the channel segment in question by the application of an electric field through that channel segment, which is referred to herein as "electrokinetically driven flow." Examples of pressure sources include negative and positive pressure sources or pumps external to the channel segment in question, including electrokinetic pressure pumps, e.g., pumps that generate pressure by electrokinetically driven flow in a pumping channel that is separate from the channel segment in question, provided such pumps are external to the channel segment in question (see, U.S. Pat. Nos. 6,012,902 and 6,171,067, each of which is incorporated herein by reference in its entirety for all purposes).

As used herein, the term electrokinetic flow is generally used to describe the movement of fluid or fluid borne material under an applied electric field. Electrokinetic flow generally encompasses one or both of electrophoresis, e.g., the movement of charged species through the medium or fluid in which it is disposed, as well as electroosmosis, e.g., the electrically driven movement of the bulk fluid, including all of its components. Accordingly, when referred to in terms of electrokinetic flow, it will be appreciated that what is envisioned is the full spectrum of electrokinetic flow from predominantly or substantially completely electrophoretic movement of species, to predominantly electroosmotically driven movement of material, e.g., in the case of uncharged material, and all of the ranges and ratios of the two types of electrokinetic movement that fall between these extremes.

As used herein, the term "flow profile" generally refers to all of the characteristics of flow of fluid or other material through a passage, conduit, channel or across a surface. Such characteristics include without limitation the flow rate, flow volume, the conformation and accompanying dispersion profile of the flowing fluid or other material, as well as other more generalized characteristics of flow, e.g., laminar flow, creeping flow, turbulent flow, etc.

II. Pressure Driven Flow vs. Electrokinetically Driven Flow

Figure 1A:
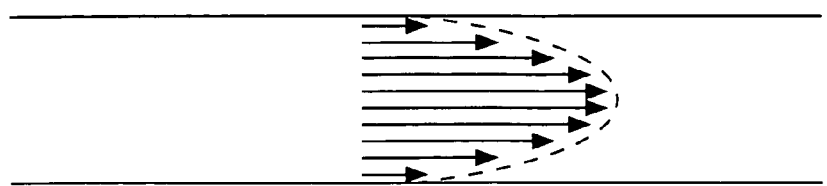
FIG. 1 illustrates a comparison between a parabolic, pressure driven flow profile (panel A) and an electrokinetically driven plug flow profile (panel B).

As noted previously, in microscale fluidic channels, pressure driven flow possesses different characteristics from electrokinetically driven flow. In particular, pressure driven flow in these systems results in parabolic flow where the fluid at the center of the passage or conduit is moving fastest, with a decreasing flow rate gradient as the fluid is closer to the side walls, with fluid at the walls being at or near zero flow rate (see schematic illustration of parabolic flow in FIG. 1A). One consequence of parabolic flow is an increase in the level of dispersion, related to the flow rate of material, which results in an increased spreading of discrete fluid or other material regions when flowing through a channel. For discussions on dispersion and Taylor-Aris dispersion in particular, see, e.g., Taylor et al., Proc. Roy. Soc. London, (1953) 219A:186–203, Aris, Proc. Roy. Soc. London (1956) A235:67–77, Chatwin et al., J. Fluid mech. (1982) 120: 347–358, Doshi et al., Chem. Eng. Sci. (1978) 33:795–804, and Guell et al., Chem. Eng. Comm. (1987) 58:231–244, each of which is incorporated herein by reference in its entirety for all purposes.

This increased dispersion can result in a decrease in resolution of analyses in microfluidic scales (resulting from dispersion of otherwise resolved species) as well as an increase in the amount of time required for a given analysis (resulting from greater required spacing between different fluid or material samples). While pressure driven flow has disadvantages of increased dispersion, it includes advantages of higher speed flow, as well as lacking any electrokinetic biasing effects resulting from an applied electric field on differentially charged species traveling through the channels of the device.

Figure 1B:
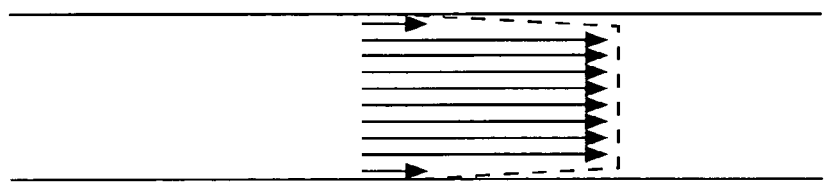

In contrast to the characteristics of pressure driven flow, electrokinetically driven flow, and particularly electroosmotically driven flow results in a "plug" flow profile where the majority of fluid is traveling at the same rate through a conduit, with only a small amount of fluid at the sheath layer moving at a slower rate or approaching a zero flow rate (see schematic illustration of plug flow in FIG. 1B). Plug flow results in substantially reduced level of dispersion, permitting higher resolution transport of discrete material regions through conduits, and higher resolution of resolved species. As noted above, however, electrokinetically driven flow can result in electrophoretic separation or biasing of differentially charged species that are transported in this way. For many analyses, e.g., those that rely on charge or size based separations of mixtures of materials, electrophoretic separation is advantageous. However, for analyses or other operations that rely on the bulk movement of complex mixtures of molecules, electrophoretic biasing can yield less optimal analytical conditions and/or difficult to interpret data.

In analytical operations, there are a number of circumstances in which one would like to maximize advantages and minimize disadvantages of each of the different flow profiles at different points in a given operation. The present invention provides a means for doing this.

IV. Hybrid Flow Profiles and Devices/Systems for Hybrid Operation

Despite the different characteristics of pressure and electrokinetic flow profiles, and in some cases, because of these different characteristics, it is desirable to be able to provide both flow profiles in a single connected channel network. For example, copending PCT Publication WO 02/10732 describes channel networks that generally achieve this end by substantially isolating one region from another in terms of flow, through the use of high flow resistance connector channels. In particular samples are drawn into the device via application of a negative pressure to a sample introduction channel. A portion of the sample material is injected into a separation channel via a high flow resistance connecting channel. By incorporating a high flow resistance connecting channel, one can effectively decouple the electrokinetically driven separation channel from the pressure driven sample loading channel. Despite the utility of the described system, it would generally be desirable to accomplish these goals in a simpler channel network without the need for substantially isolating the different channel segments from each other, e.g., through a high resistance channel segment.

In the context of high-throughput screening operations, to prevent the sample biasing effect caused by electrokinetic injection or loading, sample plugs are drawn into the device through a sample introduction channel using pressure driven flow. Pressure driven flow is also used to move these plugs through a network of interconnected channels toward a waste reservoir at which a vacuum is applied. For many applications, an electric field is also applied in at least a portion of the channel network to provide electrophoretic separation of species having different electrophoretic mobilities, e.g., based upon charge differences. The electric field creates electroosmotic flow in addition to the pressure driven flow. While electrokinetic flow has the advantage of a plug flow profile with minimum dispersion, the presence of pressure based flow, still imparts the negative effects of Taylor dispersion. Therefore, in order to perform operations, e.g., high throughput screening of pharmaceutical compounds, with higher resolution the dispersive contribution of pressure driven flow should be minimized. While elimination of all pressure driven flow could accomplish this goal, the practicalities of high throughput operations, e.g., the need for rapid flow without excessive electrophoretic biasing of materials often requires that at least a portion of the flow of materials be driven by pressure based systems.

The present invention generally provides hybrid methods and systems that utilize pressure driven flow in a first channel segment while providing substantially electrokinetically driven flow in another connected channel segment. Given the interconnected nature of microfluidic channel networks, combining two different flow types together in one interconnected channel structure has been undesirable, as it is difficult to completely separate the control of each aspect from the other. Surprisingly, however, the present invention presents methods and systems for providing an interconnected channel network wherein different segments of the channel network have independently controllable flow profiles, one that is pressure driven and another that is electrokinetically driven. Additionally, the present invention provides devices wherein the independently controlled flow profiles are manipulated to direct flow of a selected charged species from a mixture into a separate channel segment whereby the selected charged species is extracted out of the mixture.

The systems and methods of the invention are particularly useful in transporting fluids or other materials where it is desirable to capitalize on the advantages of pressure based flow during one portion of the overall operation and electrokinetic flow during another portion of the operation. By way of example, the hybrid systems of the invention are particularly useful for carrying out analyses that require rapid introduction of materials into the channels of the device, but that require longer separation, reaction or incubation times that can give rise to increased dispersion if carried out under parabolic or pressure based flow conditions.

In many pharmaceutical target screening assays, the reaction kinetics are sufficiently slow that the typical time-frame for a microfluidic reaction is too slow to generate sufficient product for adequate detection and analysis. In particular, in microfluidic systems, e.g., continuous flow screening systems as described in U.S. Pat. Nos. 5,942,443, 6,046,056 and 6,267,858 (each of which is incorporated herein by reference in its entirety for all purposes), reactants, e.g., targets and substrates, ligands or the like, are flowed into and through a reaction channel past a detection window at which point the products of the reaction are observed. Periodically, test compounds, e.g., candidate compounds from a pharmaceutical candidate library, are introduced into the flowing stream, and the effect of those compounds on the reaction are observed. In order to increase the amount of reaction time requires either reducing the flow rate in a channel of given length, or increasing the length of the channel under a given flow rate. In either event, where flow is pressure driven, it can yield substantial dispersion that is related to the amount of time of transit. Increased dispersion reduces the throughput of the system by requiring more spacing between serially introduced test compound plugs.

By passing reaction mixtures, including test compounds, from a pressure based flow to an electrokinetic flow, one can substantially increase the time of reaction by designing a channel network that permits longer time for reaction under electrokinetic flow conditions, without significantly increasing dispersion of the test compound plug. Specifically, Taylor-Aris dispersion is no longer a factor in the spreading of the test compound plugs, and only molecular diffusion remains.

The hybrid systems are also useful in operations that require rapid movement of materials, either before or after an electrophoretic separation step, e.g., in the introduction of materials to be separated, or the movement of separated species to a detection region of the channel network. In particular, sample materials can be brought into a channel network by pressure and then subjected to an electrophoretic separation step without pressure induced influences on the separating species, and without requiring a completely separate channel structure to inject an aliquot of material into a separate electrophoretic separation channel, see, e.g., PCT Publication WO 02/10732, which is incorporated herein by reference in its entirety for all purposes. Similarly, post electrophoretic separation operations can be carried out under pressure flow conditions prior to detection.

By way of example, typically when material is brought into the separation conduit under pressure based flow, that pressure flow continues while an electric field is applied across the flowing material. Because of this pressure flow, the material being moved through the conduit, including species bands that are electrophoretically separating under an applied electric field, are subjected to Taylor-Aris dispersion, which can reduce the resolution of the separation operation. To minimize this dispersion, one could try to move the material through the channel faster under higher pressure, to reduce its residence time. Unfortunately, this also results in a reduction of separation resolution, resulting from the reduction in separation time. Alternatively, one could move the sample through at lower velocity and lower pressure to increase the separation time, but this has the converse result of increasing the residence time under parabolic flow conditions, and results in increased Taylor-Aris dispersion. In either instance, gains made by altering one parameter are substantially lost by sacrifices to the other parameter. By decoupling the pressure-based and electrokinetic flow profiles, as encompassed by the instant invention, one can increase pressure based flow, e.g., for injections, to reduce residence times. Further, because the pressure flow is not linked to the electrokinetically driven flow region or channel, it has no effect on the length of time that the material may be subjected to separation. Similarly, as the material being separated is not driven by any pressure flow, one can prolong separation without the consequences of increased dispersion.

As noted above, post separation processes are also optionally performed in systems configured as described herein. For example, electrophoretically separated proteins can be labeled with antibodies, without altering their relative separation, because that labeling takes place after electrophoretic separation of the proteins. When attempted under electrokinetically driven movement, antibody labeling can substantially alter the electrophoretic mobility of a protein, thus rendering the separation largely ineffective. While described in terms of antibody labeling, it will be understood that this method is particularly advantageous for any post separation modifications that alter the mobility of the modified molecule, e.g., based upon size, charge or conformation.

For ease of discussion, hybrid systems will generally be described in terms of rapid, pressure-based introduction of materials into the channel network, followed by electrokinetic movement of materials. It will be appreciated however, that the different flow profiles of these hybrid systems may occur in either order, e.g., pressure followed by electrokinetic or electrokinetic followed by pressure, or with more than two regions having the different flow profiles, e.g., pressure/electrokinetic/pressure. Additionally, it will be appreciated that different channel segments may merely be adjusted in terms of the ratio of pressure based flow and electrokinetically driven flow as compared to other, coupled channel segments, e.g., shifting from a predominantly pressure driven flow profile to a predominantly electrokinetically driven flow profile, or less substantial shifts in that ratio.

Figure 2:
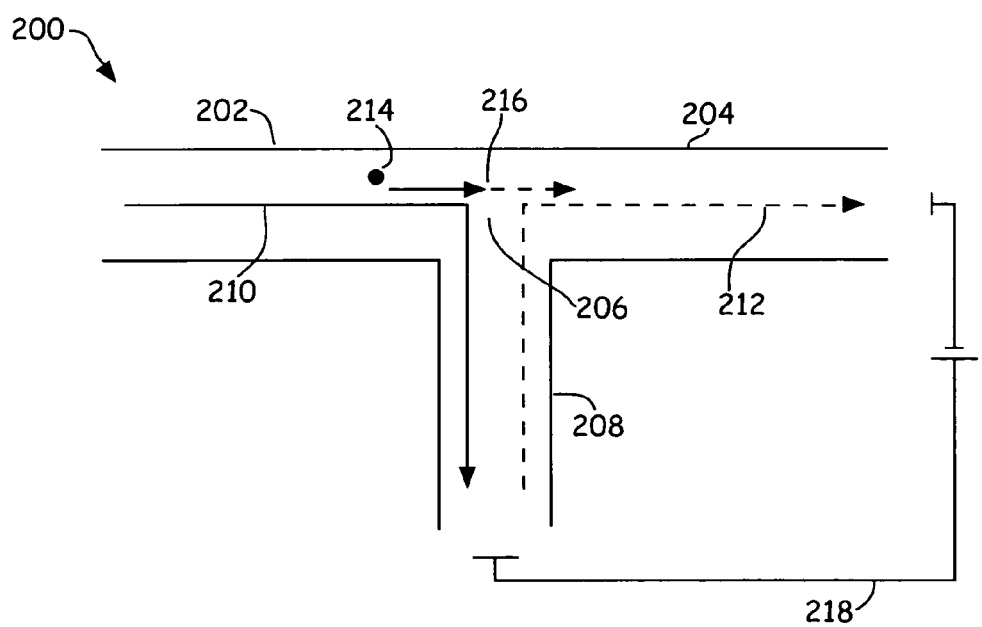
FIG. 2 schematically illustrates a hybrid or mixed mode, pressure and electrokinetically driven microfluidic channel system in accordance with the present invention.

An exemplary channel network is shown in FIG. 2. As shown, the network 200 includes a first channel segment 202 having first and second ends, that is coupled to a second channel segment 204 having first and second ends at a first fluid junction 206. Although referred to herein as "ends" it will be appreciated that an end to a channel segment is somewhat arbitrary and may be but does not require an actual termination of a channel. Thus, a channel segment end can include a transition from one channel segment to another channel segment, which channel segments can be colinear and/or otherwise undifferentiated. A third channel segment 208 is also connected at one end, to the fluid junction 206. The third channel segment 208 functions as an access channel to provide a path to tap-off or add pressure or electrokinetic forces to the first and second channel segments.

In operation, a pressure differential is applied between the first end of the first channel segment 202 and the access channel 208 (as indicated by the solid arrow). A voltage gradient is applied between the second end of the second channel 204 and the access channel 208 by electrical system 218, resulting in flow from access channel 208 which counters, to at least some extent, the flow into the access channel 208 from the first channel segment 202, resulting from the pressure driven flow. In some cases, the electrokinetic flow completely counters any hydrodynamic flow in channel 204, e.g., flowing back into channel 208. Alternatively, an additional pressure or vacuum source may be applied to the end of channel segment 204 to counter any hydrodynamic flow within this channel. In particularly preferred aspects, the electrokinetically driven flow from the access channel 208 is adjusted to substantially completely counter the pressure driven flow into the access channel 208, e.g., from channel segment 202, in order to ensure that materials traveling through the first channel move smoothly into the second channel segment 204, e.g., through junction 206 without moving into the access channel 208, and that fluid in the second channel segment 204 is not affected by the pressure differential. As noted previously, this is optionally, or additionally accomplished through the application of pressure, positive or negative to the end of channel segment 204.

The electrokinetic flow rate through channel segments 208 and 204 is dictated by both the level of charge on the channels' surfaces in the particular fluid disposed in the channel, as well as the level of the electric field applied through the channels. The surface charge in the given fluid is also termed the zeta potential of the surface. As noted previously, the level of electroosmotic flow in the channel network may be configured to cancel out the level of pressure based flow. Alternatively, electroosmotic flow may be reduced, while relying on electrophoresis to transfer one or more different species from channel segment 202 to segment 204. Reduction of electroosmotic flow may be accomplished by selection of channel and/or fluidic materials to have low zeta potentials, or by incorporating surface modifying agents into the channels, such as coating polymers and the like. A variety of different materials for fabricating low EO flow channels are described in U.S. Pat. Nos. 5,885,470, 6,156,181 and 6,238,538, each of which is incorporated herein by reference in its entirety for all purposes, while a variety of different surface modifying polymer solutions are described in, e.g., U.S. Pat. Nos. 5,948,227 and 6,042,710, each of which is incorporated herein in its entirety for all purposes.

Figure 3:
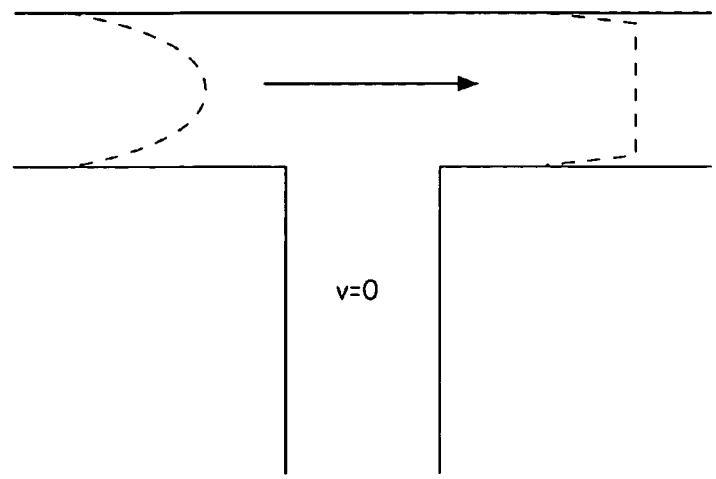
FIG. 3 schematically illustrates the flow profiles in each of the channel segments in the network shown in FIG. 2.

FIG. 3 schematically illustrates the flow profiles in each of the first and second channel segments 202 and 204, respectively. As shown, in the first channel segment 202, the pressure driven flow results in parabolic flow while the electrokinetic flow in the second channel segment 204 results in plug flow. The access channel 208 is shown with no net flow, assuming that the pressure flow in and electrokinetic flow out of the access channel 208 results in a net zero flow rate.

The ability to separately control the level of pressure and/or electrokinetic flow in fluidly connected channels has a wide variety of different uses that range from the outright separation of electrokinetic flow profiles from pressure driven flow profiles in interconnected channels, to modest variations in relative ratios of electrokinetic and pressure driven flow within interconnected channels.

Exemplary applications of the systems and methods of the invention include separations based analyses that require extended separation times, e.g., separations of minimally different species, post separation reactions that would affect electrophoretic mobilities of the separated species, or movement of materials over longer distances, where the materials do not include readily electrophoretically biased materials, e.g., having widely varying charges amongst the different species in the material.

One example of a system that is particularly benefited by the present invention are serial input microfluidic high throughput pharmaceutical screening systems, and particularly those that perform a mobility shift based detection scheme. In brief, these systems serially introduce discrete slugs of pharmaceutical test compounds into a flowing stream of target reactants, to determine an effect, if any, of the test compound on the interaction of the reactants. Typically, these reactants can include enzyme substrate pairs, receptor ligand pairs or other complementary binding pairs, cells or the like (see, e.g., U.S. Pat. No. 6,046,056). Identification of an effect and correlation of that effect to a particular test compound is typically facilitated by maintaining spacing between different test compounds as they flow through the channels of the system. In the case of certain reactions, the only indicia of the progress of a reaction, even with labeled reactants, is a shift in the level of charge of a labeled reactant, which produces a shift in the labeled reactant's electrophoretic mobility. Examples of such reactions include, e.g., phosphatase and kinase reactions where addition or removal of a phosphate group alters the charge of the substrate relative to the product. A number of other reactions fit this conformation or are readily configured to fit this configuration, including, e.g., protease assays, nucleic acid assays using uncharged labeled analogs, i.e., PNAs, etc.

Likewise, in systems that require extended reaction times, maintaining separation between adjacently introduced plugs becomes more difficult as dispersion increases with the extended flowing time. Accordingly, spacing must be increased between test compounds, reducing the rate of throughput for the system. However, by transitioning the flowing stream of reactants and test compounds to an electrokinetic or electroosmotic flow profile, one can increase the flow time without correspondingly increasing dispersion, thereby allowing one to maintain the spacing or pitch of adjacently input test compound plugs, and thereby preserve throughput.

Figure 4:
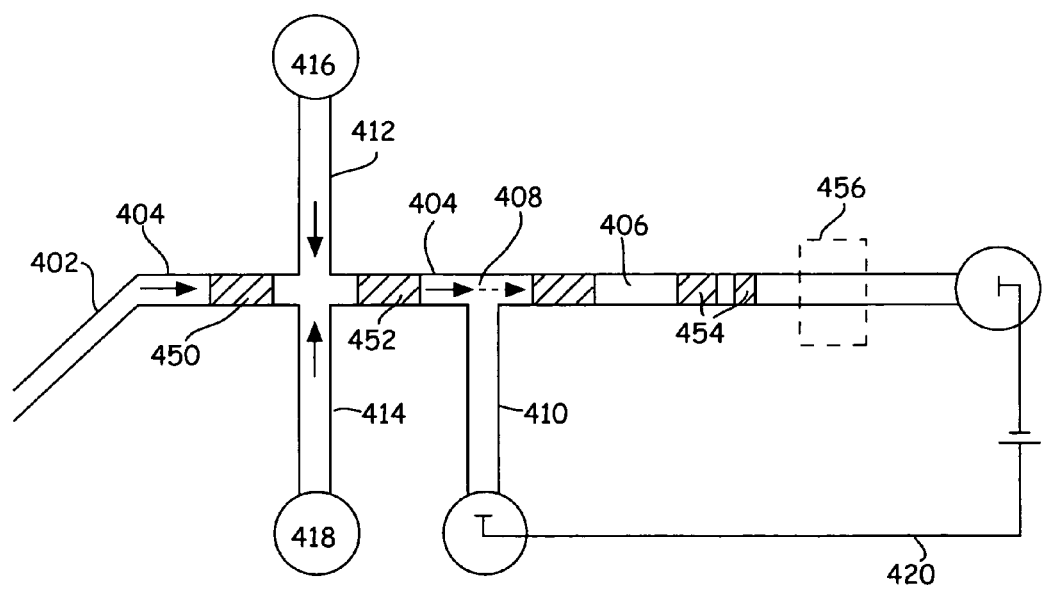
FIG. 4 schematically illustrates a device according to the present invention in operation performing a serial screening assay that utilizes a separation based analysis following sample introduction.

Briefly, test compounds are brought into the system by a sampling system, e.g., a pipettor element integrated into a microfluidic device, by applying a vacuum to the system to draw in the test compounds. Application of the same vacuum that draws sample plugs into the chip also draws reaction components, e.g., enzyme and substrate from different wells integrated onto the chip and connected to a main channel via side channels. The reagents mix in the main channel and are mixed with the different sample plugs in discrete reaction plugs. After a predetermined incubation or reaction time, the reaction mixture plugs may be transitioned to an electrokinetic flow profile in accordance with the invention where they will migrate substantially only under the applied electric field, until they move past a detection point. The applied electric field allows for electrophoretic separation of species without a concomitant decrease in resolution resulting from Taylor dispersion. In alternative aspects, the material may be transitioned back to a pressure based flow profile prior to detection or some other manipulation of the material.

a. Flow Profile Hopping:

An example of a continuous flow assay format utilizing a mobility shift detection scheme is schematically illustrated in FIG. 4. In this assay format, the reagents for the assay, e.g., a substrate and an enzyme, or complementary binding partners, i.e., receptor/ligand or nucleic acids, typically include a labeled reactant that undergoes a charge change during the reaction, e.g., a charged moiety is added or removed from the labeled reagent. By way of example, in a typical kinase assay, a labeled kinase substrate is contacted with a kinase enzyme that adds a highly charged phosphate group to the substrate yielding a substantial change in the charge of the product relative to the substrate. The charge difference is used to separate the product from the background substrate level. The reagents are continuously flowed along a fluid channel whereby the steady state level of the reaction yields a constant signal that is a result of continuously reacting and separating reagents. When an effector of the reaction in question is introduced into the reaction, e.g., in a slug, it perturbs the steady state reaction/separation, yielding an indicative variation or signature in the level of signal detected from the channel. Continuous flow mobility shift assays are generally described in U.S. Pat. Nos. 5,942,443, 6,046,056 and 6,267,858, the entire contents of which are incorporated by reference herein.

In the context of the present invention, and with reference to FIG. 4, an exemplary assay device 400 includes a sampling element 402, e.g., a pipetting capillary attached to a microfluidic device, that is in fluid communication with a first channel segment 404. First channel segment 404 is coupled to second channel segment 406 at a first fluid junction 408 at which third channel segment 410 is also fluidly coupled. The intersecting channels form the basic control structure as illustrated in FIG. 1. In operation for a mobility shift based pharmaceutical screening assay, assay reagents are introduced into channel segment 404 from side channels 412 and 414 which are coupled to reservoirs/reagent sources 416 and 418, respectively.

Again, with reference to FIG. 4, test compounds 450 are sampled as fluid slugs through the sampling element 402 and moved into channel segment 404 under pressure driven flow. In channel segment 404, the test compound 450 mixes with the reagents from reservoirs 416 and 418 and interacts with those reagents in a slug of reaction mixture 452 such that if the test compound is an effector, e.g., an inhibitor, of the reaction of interest, the test compound will alter the level of the reaction. In the case of the above described kinase reaction, an inhibitor would result in less charged product being produced.

As the reaction slug of interest (e.g., that containing the test compound) moves into first fluid junction 408, it transfers from pressure driven flow to electrokinetically driven flow. In particular, by adjusting the level of electrokinetic flow moving into channel segment 406 to match the level of pressure driven flow coming out of channel 404, one can ensure a seamless hand-off of materials from channel segment 404 to channel segment 406 through fluid junction 408.

Once the reaction mixture moves into channel segment 406, it is subjected to electrokinetic forces, e.g., via electrical control system 420, that at once move the fluid through the channel segment and electrophoretically separate differentially charged species in the reaction mixture as shown by separated species 454. Because the system is a continuously flowing system, electrophoretic separation is largely unnoticeable at a steady state. This is because product that moves, e.g., faster than substrate, will simply overtake slower moving, adjacent substrate, resulting in no effective net change in the level of product and substrate at a given location. However, where the test compound disturbs the steady state reaction, it results in a localized increase or decrease in the level of product produced. The electrophoretic mobility of the increased species relative to steady state, e.g., product or substrate, yields a concentration of detectable label either before or after the slug of reaction mixture that contains the test compound. For example, where a test compound is an inhibitor of a reaction, the slug of inhibitor will produce a localized increase in substrate. The difference in electrophoretic mobility of substrate to product will yield a deviation in the steady state label, e.g., as an increase or decrease in signal at the detection window 456.

In optional cases, the electrokinetically driven flow out of channel 410 into channel 406 may be more or less dominated by electroosmotic flow. In particular, if the electrophoretic mobility of the species of interest is sufficiently high to overcome a pressure flow countercurrent, then a lower electroosmotic flow rate could be used, although this would result in greater levels of dispersion.

Similarly, if one is performing an assay that requires enhanced sensitivity, one could adjust the level of the different flows such that a substrate that has less charge than a product is preferentially siphoned from channel segment 404 into segment 410, and thus prevented from entering channel 406. Meanwhile, the elevated charge and electrophoretic mobility of the product permits that product to preferentially migrate into channel segment 406 where it can be detected in the absence of the labeled substrate background, thus increasing the sensitivity of the assay. See, e.g., copending U.S. patent application No. 60/309,113 filed Jul. 31, 2001, which is incorporated herein by reference in its entirety for all purposes. This is particularly useful for assays that use enzyme reactions with slow kinetics, etc.

b. Selective Ion Extraction:

The devices of the present invention are also useful for separating differently charged species from a sample mixture by managing the flow profiles of the various species by controlling the applied pressure or electric field, or alternatively by controlling both the applied pressure as well as the electrical field. Using a fluid control system with multiple pressure and voltage sources, the pressure and/or voltage in any given channel segment of the device can be controlled such that the hydrodynamic flow and electric field in any section of the microfluidic channel network can be set to desired values. The present invention provides devices wherein the fluid flow in different segments of the channel network is independently controlled by overlapping the two different flow profiles, i.e., pressure based and electrokinetically driven, and simultaneously controlling the flow velocity under each of the flow profiles to achieve a net velocity for a given species contained in the fluid to an amount sufficient to facilitate separation and isolation of the differently charged species contained in the fluid-borne sample. Thus, mixtures of two or more sample species (e.g., a neutral substrate and a negatively charged product of an enzymatic reaction as illustrated below in Example 1) having different electrophoretic mobilities sent into a channel intersection, such as a T-intersection as described below, can be separated completely into separated components in separate channels of the intersection based on the different electrophoretic mobilities of the sample species.

In particular, the separation of a given species is achieved by counterbalancing its pressure-driven or hydrodynamic flow velocity with its electrophoretic velocity to direct its flow in a given direction whereby a species with one electrophoretic mobility is separated and flowed into a first region of a device while a second species with a second electrophoretic mobility is flowed into a second region of a device. The hydrodynamic or pressure-driven velocity of a species is its flow velocity due to pressure induced flow. Electrophoretic velocity for a species is its electrophoretic mobility ($\mu_{ep}$) multiplied by the applied electrical field. In embodiments employing overlapping pressure based flow with electrokinetic flow in a given channel segment, the net velocity of a species or material traveling in that channel segment is the sum total of its hydrodynamic flow velocity and its electrokinetic velocity. The following example illustrates the computation of net velocity of a given species in a channel region.

For example, if species A is subjected to a pressure of $-1$ psi resulting in a hydrodynamic flow velocity of 0.1 cm/s and a electrophoretic mobility ($\mu_{ep}$) $1.4 \times 10^{-4}$ cm$^2$/V–sV with an electric filed (E) of 2000 V/cm, and in the same direction as the hyrdrodynamic flow, then the net flow of the species will be as follows:

Net Flow=Hydrodynamic flow velocity+[electrophoretic mobility $(\mu_{ep})\times E$]

Net Flow of $A$=0.1 cm/s+0.28 cm/s

Net Flow of $A$=0.38 cm/s

The present invention allows the manipulation of the flow velocities of multiple fluid borne species by controlling the applied pressure and applied electric field at various channel segments of an interconnected channel network to thereby separate a given species. FIG. 7 schematically illustrates a device and its operation for an enzyme assay wherein a charged species is continuously separated by multiport pressure and voltage control. Device 700 includes a main channel having a first end connected to a sample source 702 and a second end terminating in waste reservoir 728. The main channel comprises channel segments 702, 705 and 706. Side channels 714 and 716 intersect the main channel at channel segment 702. Side channel 704 intersects the main channel at channel segment 705 and terminates into reservoir 726. During operation, a series of sample plugs, such as for e.g., fluid borne inhibitors of the substrate and enzyme interaction are drawn into the main channel through the sample source 720, e.g., a pipetting capillary or a reservoir, by applying a negative pressure at reservoir 726 (or other reservoir in the channel systems such as reservoir 728). Assay reagents are introduced into channel segment 702 from side channels 714 and 716 and interact with the sample within segment 702 to form a mixture comprising differently charged species. For example, in an enzyme assay, such as a kinase enzyme assay, the assay reagents comprise an enzyme and a substrate and they interact in the presence of a test compound to form a mixture comprising a product, enzyme and substrate whereby the product and the substrate have a different charge and therefore different electrophoretic mobilities. The sampling of the sample plugs and the flow of the assay reagents into the main channel is achieved by applying a negative pressure at reservoir 726 and by maintaining the pressure at reservoirs 722, 724 and 728. The net velocity of each of the different species contained in the fluid mixture in channel segment 702 is equal to the hydrodynamic velocity induced by the combination of pressures applied at all the reservoirs. However, once the fluid mixture enters junction 705, it is also subjected to an electric field created by a voltage gradient applied at reservoirs 726 and 728. The voltage gradient creates an electric field in channel segments 704, 705 and 706. Non-equal electrophoretic mobilities of the substrate and product molecules at junction 705 results in a finite difference in the net velocity of both the product and the substrate causing their separation. Almost instantaneously, the separated species are further diverted apart by modulating the pressure applied at reservoir 726 whereby the species having an electrophoretic mobility below a given value will be separated and diverted into channel segment 706 while all the species having an electrophoretic mobility greater than the given value will flow into channel segment 704. Alternatively, the electric field applied at reservoir 726 will be modulated such that the species having an electrophoretic mobility above a given value will be separated and directed into channel segment 704 while all the species having an electrophoretic mobility below the given value will flow into channel segment 706.

To better understand the teachings of the present invention, the separation of the differently charged species at fluid junction 705 is described in more detail below. As shown, the T-intersection channel network includes segments 702, 704 and 706 which meet at a common intersection or fluid junction 705. Each of the channel segments are connected to fluid ports or reservoirs, or to an external sampling element as described above and shown in FIG. 7A. A multiport pressure and voltage controller is used to control the applied pressure and applied electric fields at each of the different reservoirs or fluid ports connected to each of the channel segments. For clarity, a subscript notation is used to reference the voltage and pressure applied across each channel segment, e.g., $V_1$ and $P_1$ refer to the voltage and pressure applied across channel segment 702, $V_2$ and $P_2$ refer to the voltage and pressure applied across channel segment 704, etc. By using a multiport module capable of providing independently controlled pressure and voltage to the individual channel segments, the systems of the invention allow one to control the flow patterns within each channel segment whereby all species having an electrophoretic mobility ($\mu_{ep}$) above a certain amount flow in one direction and all the species having an electrophoretic mobility ($\mu_{ep}$) below that same amount flow in a second direction.

Figure 7A:
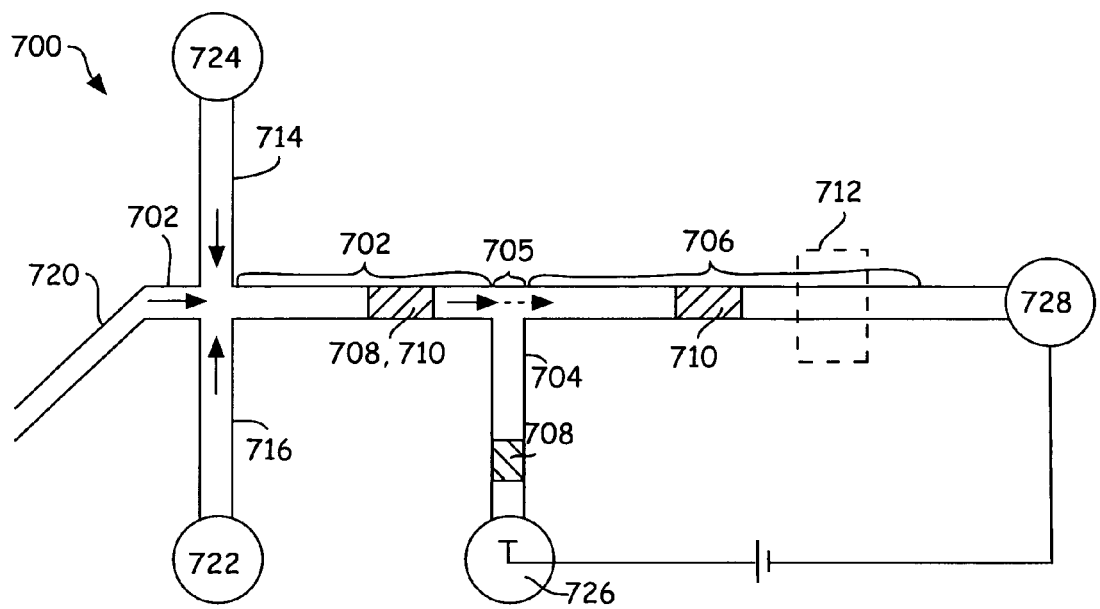
FIG. 7, panels A–D provide a schematic illustration of a system for performing selective ion extraction.
Figure 7B:
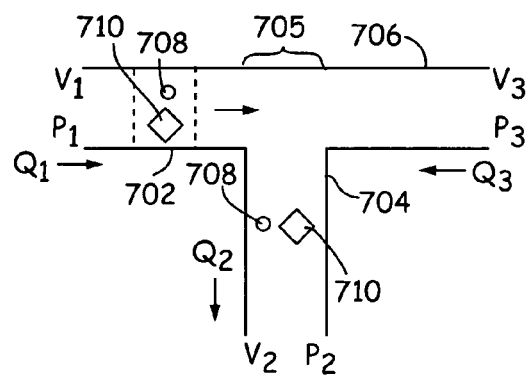

FIGS. 7B, C and D further illustrate the effect of multiport pressure and voltage control on the flow of differently charged species 708 and 710. Certain assumptions are made herein, such as, for example, species 708 is assumed to have a zero charge (e.g., Z=0) while species 710 is assumed to be highly negatively charged (e.g. Z=−2). Although these assumptions are made herein for the purposes of simplicity and clarity, it is to be noted that the principles of selective ion extraction may be applied for separating any species from a mixture as long as the species are differently charged or alternatively as long as the species have the same charge but have a different mass. A different charge encompasses positive versus negative charge, a high positive charge versus a low positive charge as well as a high negative charge versus a low negative charge.

Further, the electrical conductivity of the bulk fluid is assumed to be uniform throughout the T-intersection channel network. In addition, the electroosmotic flow is preferably minimized or neutralized by, for example, providing an appropriate surface coating to the channel walls so as to suppress the build-up of surface charge on the channel walls as described previously. However, it is to be understood that the present invention could also be used under electroosmotic flow conditions. Under these assumptions, a pressure driven flow of species 708 and 710 is established by setting P1=P, P2=0 and P3=P/2. The corresponding flow rates Q in each of the channel segments 702, 704 and 706, respectively are then Q1=−Q2 and Q3=0. In other words, all of the fluid entering the channel network through channel segment 702 would then exit through channel segment 704, and thus both species 708 and 710 would enter channel segment 704 as shown in FIG. 7B. Similarly, an electric field may be established between channel segments 704 and 706 by applying, for example, V2=V, V3=0 and V1=V/2. The voltage V1 can be set by applying the appropriate voltage to any one of the reservoirs 722, 724, or to a reservoir (or capillary element) which is fluidly coupled to channel segment 720. Upon entering the intersection 705, the fluid mixture is subjected to an electric field due to the voltage gradient created by V2 and V3. Therefore, the fluid species will now experience a net flow that is based upon the combination of pressure induced flow as well as electrokinetic flow. In other words, depending on the ratio of the average hydrodynamic velocity ($V_p$) of a species to its average electrophoretic velocity ($V_{ep}$), the species will be transferred completely to channel segment 704 or 706 or may be split between channel segments 704 and 706. It should be appreciated that although the present description is made in reference to varying pressure settings at the various channel segments, it is not the intent to limit the invention in this regard. Variations may be made to voltage or pressure or both voltage and pressure to achieve similar separations.

Figure 7C:
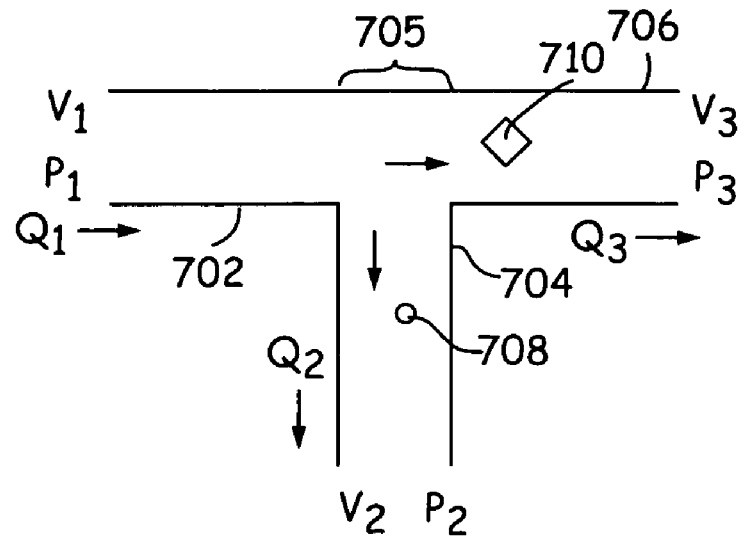
Figure 7D:
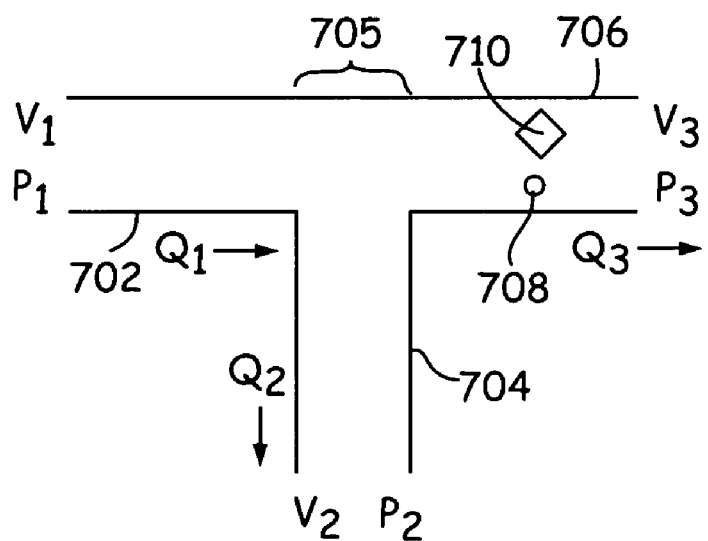

For example, as one non-limiting example of the teachings of the present invention, FIGS. 7B–D are schematic diagrams of the T-intersection of channel network shown in FIG. 7A wherein the pressure applied on the side arm channel segment 704 is varied while maintaining the other parameters constant. As shown in FIG. 7B, where the pressure applied to channel segment 704 is very low, a reverse hydrodynamic velocity is established in channel segment 706 which is greater than the electrophoretic velocity of the charged species 710 such that the net velocity of species 710 is dominated by its hydrodynamic velocity resulting in the flow of species 710 into channel segment 704. Species 708 is assumed to have a net charge of Z=0 and as such its net velocity is equal to its hydrodynamic velocity causing it to also flow into channel segment 704. Therefore, both species 708 and 710 will flow into channel segment 704 and little or no species would be detected in the detection window located along channel segment 706

As P2 gradually increases towards P3, the hydrodynamic velocity in fluid junction 705 and in turn channel segment 706 decreases while the electrophoretic velocity remains constant. At some pressure setting, the electrophoretic velocity of charged species 710 will exceed its hydrodynamic velocity in the fluid junction 705 such that its net velocity will be dominated by its electrophoretic velocity causing it to flow into channel segment 706,while the uncharged (or lesser charged) species 708 will continue to flow into channel segment 704, as shown in FIG. 7C. The exact pressure setting for the transition between the flow patterns shown in FIGS. 7B and 7C depends on the net velocity of each species which as described above, is the total of the hydrodynamic velocity and electrophoretic velocity, whereby the species with the highest electrophoretic mobility would be extracted first into the channel segment 706.

It should be noted that a "separation window" is created as the pressure on the side arm channel segment 704 changes whereby only the more highly charged species 710 is extracted into the detection channel segment 706, while the species 708 with lesser charge and hence lesser electrophoretic mobility continues to flow into the side arm 704. As the pressure P2 on the side channel segment 704 further increases, the hydrodynamic flow reverses direction in that channel segment and a net forward pressure driven velocity will be created in fluid junction 705 and channel segment 706 such that both species 708 and 710 flow into channel segment 706 as is illustrated in FIG. 7D.

It is to be noted that the principles of this fluidic division technique may be applied for separating or extracting any one or more species from a mixture as long as the one or more species are charged (for a single species) or differently charged (for two or more species), or alternatively as long as two or more species have the same charge but have a different mass. For example, the teachings of the present invention may be used to extract (e.g., concentrate) a single charged species in a sample solution such as a charged molecule such as DNA, RNA, or other charged polymers, which can, for example, be extracted (and thus concentrated) in one channel segment of a T-channel intersection, for example, where such charged molecule can then be flowed to an analysis or detection region for further analysis and/or detection, or further concentrated in the device.

The teachings of the present invention are particularly useful for extracting and pre-concentrating samples typically separated by electrophoretic techniques, including charged biomolecules such as peptides, proteins, nucleic acids (e.g., DNA or RNA), and polysaccharides, as well as charged synthetic polymers and the like for further analysis, such as probing DNA for rare molecular events, as may occur in cancer screening. For example, as is more fully disclosed in co-pending patent application U.S. Ser. No 60/436,098 entitled "Single Molecule Amplification and Detection of DNA in a Microfluidic Device," filed on Dec. 20, 2002, the entire contents of which are incorporated by referenced herein, single molecule amplification can be used for the detection and statistical characterization of rare nucleic acids of interest in a sample, e.g., for disease diagnosis (e.g., cancer diagnosis), detection of pathogens, detection of rare environmental nucleic acids, and the like. For example, many individual amplification reactions can be performed on reaction mixtures derived from a sample comprising a rare nucleic acid of interest, where each reaction mixture has few (e.g., 1) or no copies of the rare a nucleic acid of interest, e.g., until the nucleic acid of interest is identified in a reaction mixture. In such applications, the ratio of wild type to mutant DNA molecules is expected to be ~100:1. When using a genotyping system to count rare events, it is desirable to process a DNA sample sipped from an external microtiter plate (or other external sample source) as quickly as possible to increase the throughput of the system.

Figure 8:
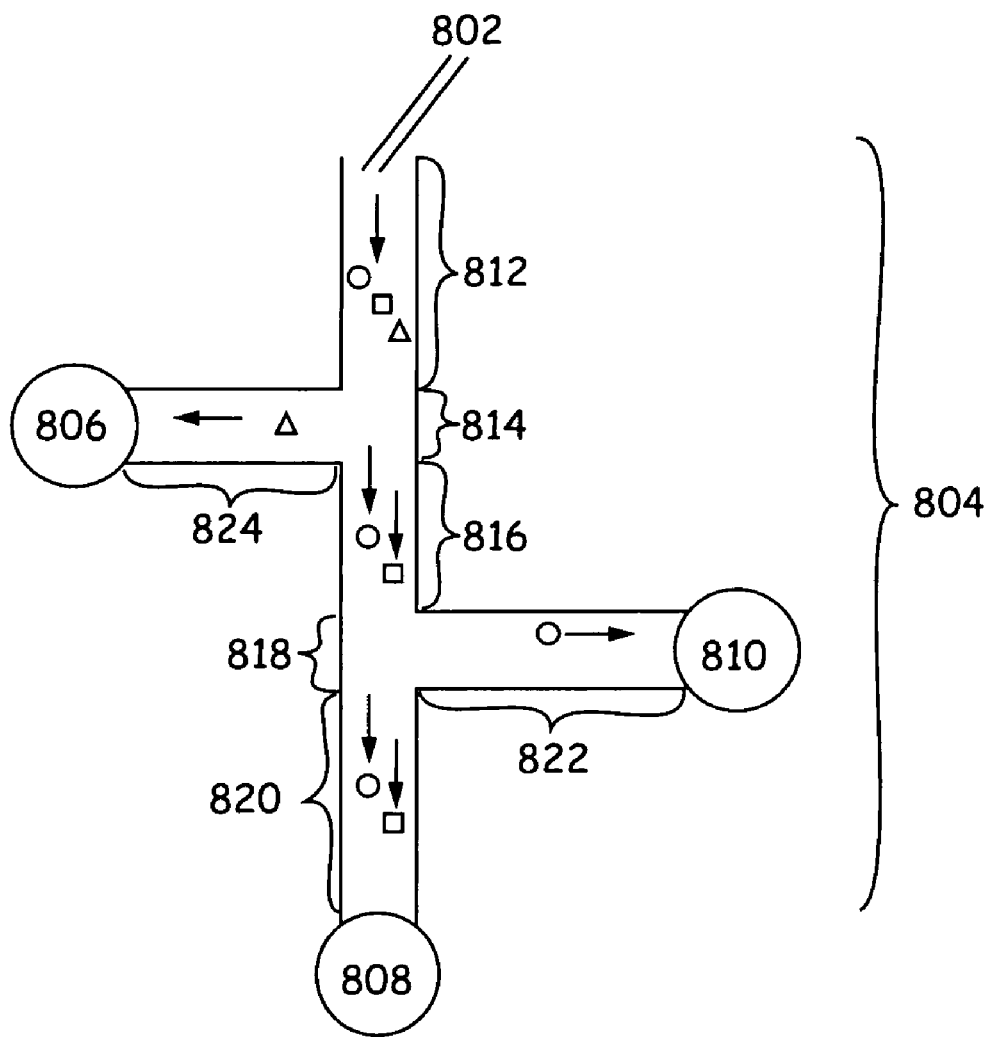
FIG. 8 illustrates multistage selective ion extraction of a charged species from a mixture using devices of the present invention wherein pressure and voltage manipulation allow extraction of a species having an intermediate charge.

High throughput amplification systems such as those embodied in high throughput microfluidic systems are particularly well adapted to performing these methods, which can be used to detect nucleic acids of interest that are present at exceedingly low concentrations in a sample to be analyzed, e.g., by performing many low copy number amplification reactions until the nucleic acid of interest is detected, and/or until enough copies of the nucleic acid of interest are detected that reliable statistical evaluations can be performed. An example of an integrated microfluidic genotyping system that can be used to detect rare nucleic acids is described in co-pending patent application U.S. Ser. No. 10/123,100 entitled "Systems and Methods for High Throughput Genetic Analysis," filed on Apr. 11, 2002, the entire contents of which are incorporated by reference herein. The system integrates reagent assembly, nucleic acid amplification, and genotyping readout all on one microfluidic chip as illustrated in FIGS. 7 and 8 of the '100 application. The reagents necessary for PCR are placed on the chip and the nucleic acid (e.g., DNA) samples to be tested are presented to the chip from a microtiter plate. The chip has a capillary attached to it and the nucleic acid samples (including both wild type and mutant DNA, for example) alternating with buffer, are brought onto the chip through the capillary. Nucleic acid samples, polymerase and other PCR reagents such as primers and probes, are pulled into the main microfluidic channel by vacuum, pressure, electroosmotic or electrokinetic flow, or the like, and all the components mix in the first few seconds after entering the main channel. They are then moved into a reaction region or channel of the chip that has metal traces on the chip that can be heated by the application of an electric current. As the reaction mixture plugs move through the reaction channel, the reaction channel is heated and cooled to amplify the nucleic acids in the sample, such as DNA. The channels of the chip are configured, and the fluid control system (e.g., vacuum) is set, so that each sample experiences a specified number of cycles of amplification. A fluorescent signal generated by the amplification is detected at the end of the flow path to detect the nucleic acid molecules in the sample.

The teachings of the present invention can be employed as a means to process a larger volume of the a sample containing one or more charged components in the microtiter plate in the genotyping system per unit time. In the genotyping chip disclosed in the '100 application and generally described above, for example, the heated (thermocycled) reaction channel has a fixed length which is calculated based on the desired number of amplification cycles to be performed in the channel, which in the described chip has a length of about 40 mm. For typical microfluidic channel geometries (e.g., chips having channel widths and/or depths less than about 200 microns, for example less than about 100 microns), this translates to a relatively low flow rate through the heated reaction channel. If there are only a few rare mutant molecules contained in a relatively large original DNA sample volume, for example (e.g., on the order of about 5 microliters) disposed in the wells of a microtiter plate, then accessing these molecules could take a very long time.

Figure 15:
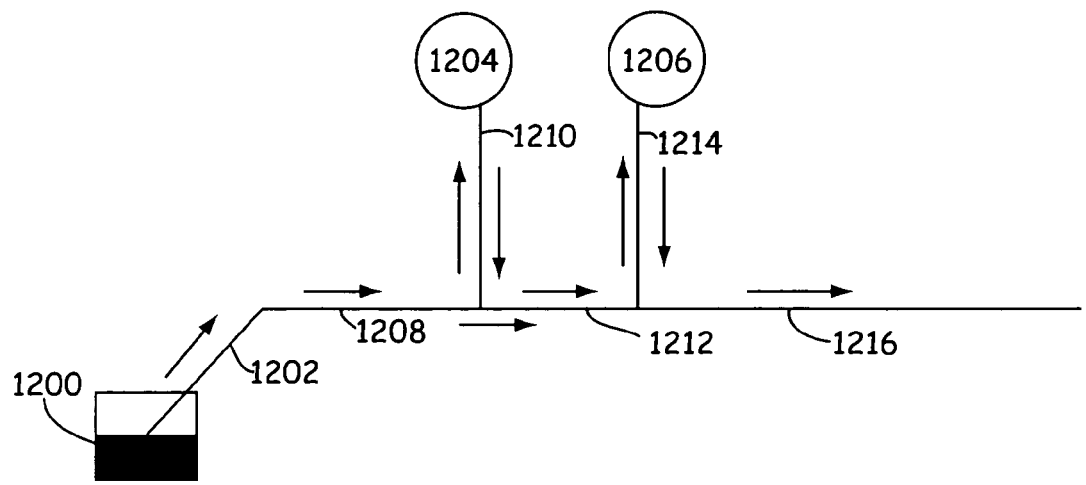
FIG. 15 is a schematic of a microfluidic device channel configuration that can employ the teachings of the present invention to extract and pre-concentrate electrophoretically mobile species (such as DNA or RNA) from a sample for further analysis in the microfluidic device.
Figure 16A:
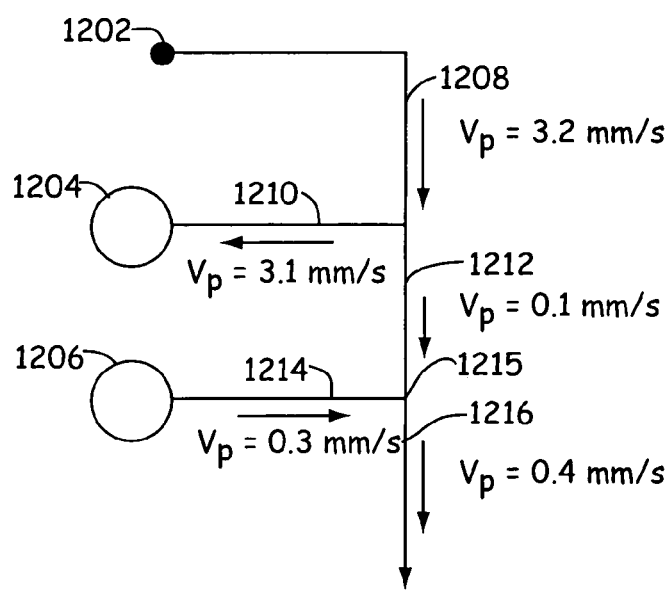
FIG. 16A is a schematic of the microfluidic device channel configuration of FIG. 15 showing an example of the pressure driven velocity through the various channel segments of the device.
Figure 16B:
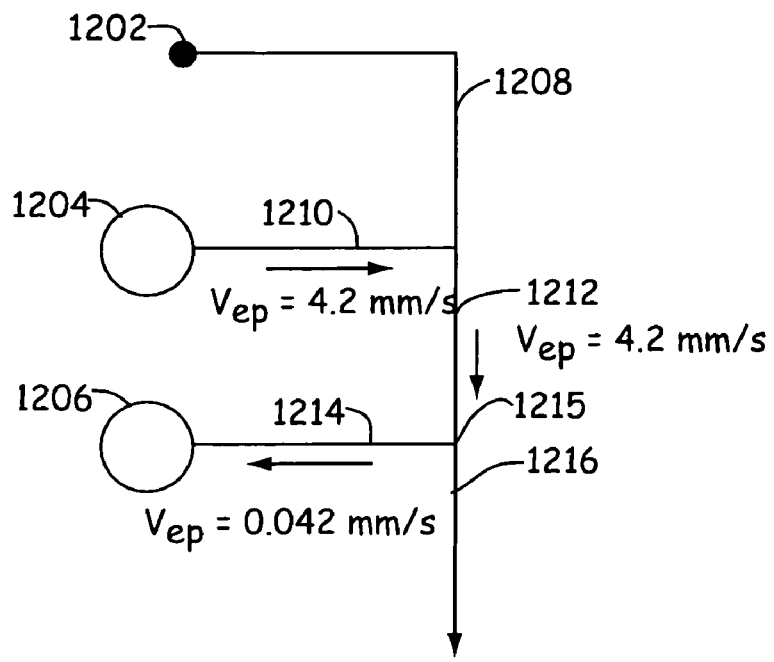
FIG. 16B is a schematic of the microfluidic device channel configuration of FIG. 15 showing an example of the electrokinetic velocity through the various channel segments of the device when an electric field is applied between reservoirs 1204 and 1206 of the device.

A microfluidic chip configuration is shown in FIGS. 15 and 16 which can be used as a front end extractor and pre-concentrator for the genotyping platform described in the '100 application, for example, in which the extraction and pre-concentration of one or more charged species in the sample (such as DNA) occurs under continuous flow prior to the sample entering the heated reaction channel. As shown in FIG. 15, patient DNA samples (or any other sample containing charged molecules) may be placed in one or more wells of a microtiter plate 1200 (such as a conventional 96, 384, or 1536 well plate commercially available) in a low ionic strength buffer having a relatively low electrical conductivity. Samples are sipped through capillary 1202 at a relatively high flow rate (for example, about 3 nl/s) by applying a vacuum to reservoir 1204 such that the bulk pressure driven flow is along channel segments 1202, 1208, and 1210 and towards reservoir 1204. It is to be noted that for planar chip configurations, capillary 1202 could be replaced with a sample reservoir into which sample is placed, and then a vacuum applied to reservoir 1204 would cause sample in the sample reservoir to flow into the channel network. At the same time, a substantially lower positive pressure or vacuum can be applied to one or more reservoirs of the device fluidly-coupled to reaction channel 1216 to set up a pressure flow in the reaction channel. For example, as described below, a slight positive pressure can be applied to reservoir 1206 (and a slight vacuum applied to a reservoir (not shown) downstream of reaction channel 1216) to set up a positive pressure flow through the reaction channel 1216 which is sufficient for thermocycling (e.g., by PCR) to occur in the reaction channel under continuous flow conditions. Thus, as shown in FIG. 16A, based on the applied pressures and/or vacuums (and the dimensions of the various channel segments), a pressure driven velocity ($V_p$) in each of the various channel segments of the chip can be established such that the pressure driven velocity is significantly higher at the front end of the device (e.g., about 3.2 mm/s in channel segment 1208) than it is in the reaction channel region of the device (e.g., about 0.4 mm/s in the reaction channel 1216). For example, the applied pressure and/or vacuum can be established, and the channel dimensions chosen, such that the total flow rate in channel segment 1208 is about twice that of the flow rate in channel segment 1216, for example, about five times the flow rate in channel segment 1216, for example about ten times or more the flow rate in channel segment 1216.

Figure 16C:
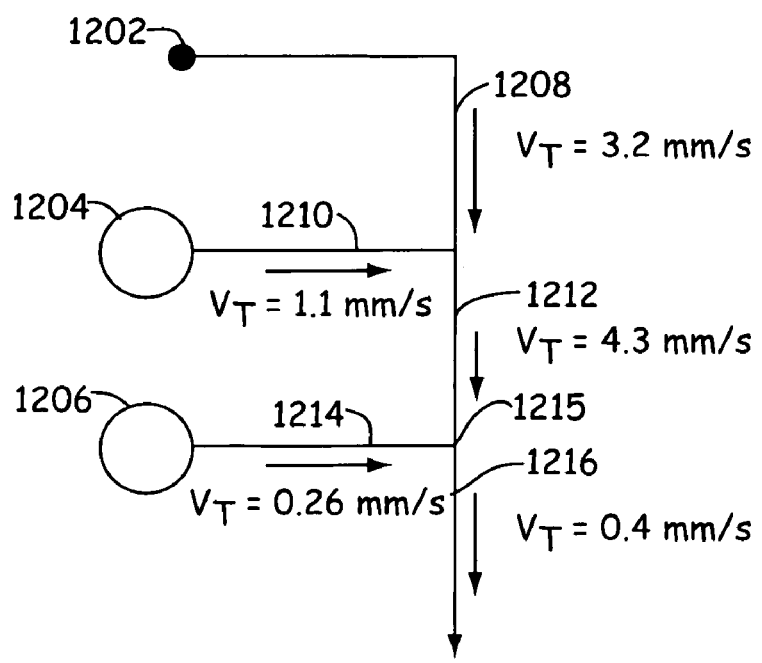
FIG. 16C is a schematic of the microfluidic device channel configuration of FIG. 15 showing the overall total species velocity through the various channel segments of the device.

Selective ion extraction is then used to extract the charged DNA from the other contents of the sample. As show in FIG. 16B, an electric field is applied between reservoirs 1204 and 1206 to prevent the DNA in the sample from following the bulk pressure driven flow path towards reservoir 1204, assuming that the electrophoretic velocity ($V_{ep}$) of the DNA is larger than the pressure driven velocity. In other words, the electric field applied between reservoirs 1204 and 1206 can be modulated such that the charged DNA in the sample will be separated and directed into channel segment 1212 while all the species having an electrophoretic mobility below the given value will flow into channel segment 1210. Thus, for example, an electric field can be established between reservoirs 1204 and 1206 whereby the electrophoretic velocity ($V_{ep}$) of the charged DNA in the sample is on the order of about 4.2 mm/s in channel segment 1210 (which exceeds the pressure driven velocity of about 3.1 mm/s shown in FIG. 16A), thus creating an overall total velocity ($V_T$) of about 1.1 mm/s which forces the DNA into channel segment 1212, as shown in FIG. 16C. Because the free zone electrophoretic mobility of DNA is approximately constant as a function of size (e.g., number of base pairs), it is not necessary to provide very fine "tuning" of the selective ion extraction process despite the possible heterogeneity of the patient sample which may contain a variety of DNA sizes.

To concentrate the extracted DNA in channel segment 1212, fluid in well 1206 is in a high salt buffer (e.g., has a relatively high electrical conductivity based on its high ionic strength) which serves two purposes: (i) it minimizes the voltage drop and hence electric field in channel segment 1214, and (ii) it establishes a high salt/low salt boundary necessary for field amplified stacking to occur at channel intersection 1215. It is envisioned that a slight positive pressure flow of the high salt fluid from well 1206 (e.g., which creates a pressure driven velocity on the order of about 0.3 mm/s in channel segment 1214 as shown in FIG. 16A) maintains the high salt/low salt boundary required for stacking to occur at channel intersection 1215 and further prevents DNA from entering channel segment 1214. Thus, the DNA in the sample will be stacked at channel intersection 1215 due to the presence of a high salt/low salt boundary at the channel intersection, and will flow at relatively high concentration under continuous flow into channel section 1216 where it can be amplified for further processing and/or detection (e.g., detection of rare nucleic acid molecules for cancer screening purposes, for example).

Figure 17:
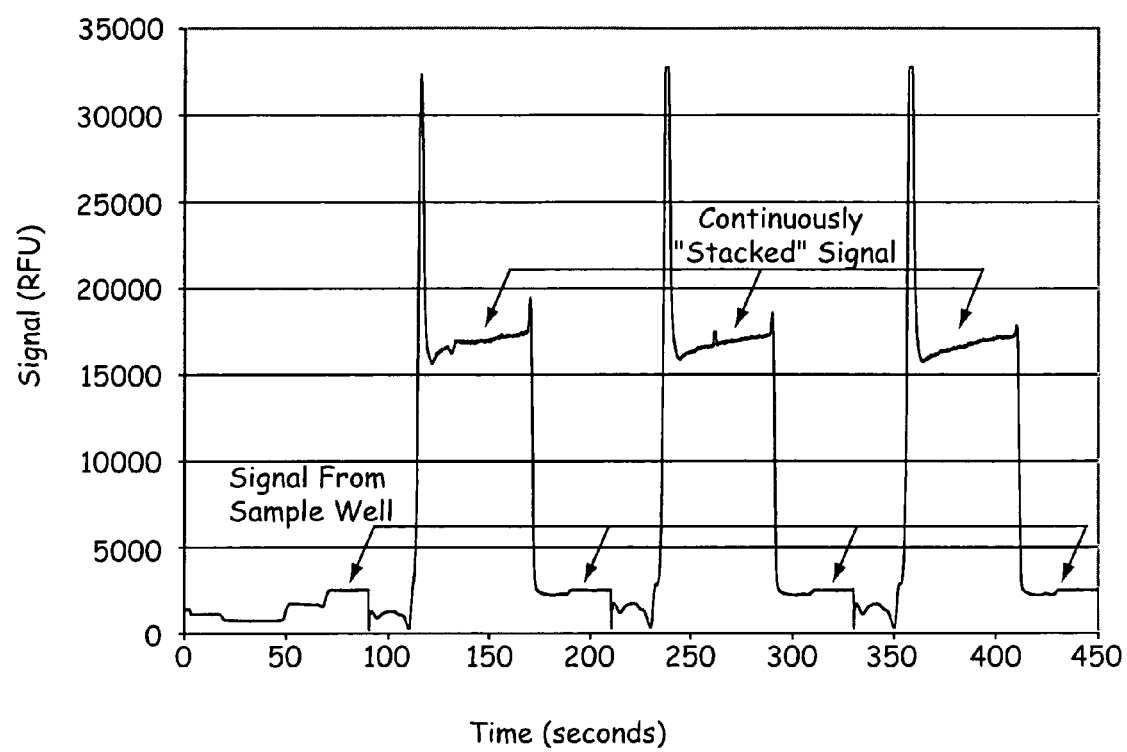
FIG. 17 is an electropherogram showing an approximate seven-fold stacking of DNA in a sample using a channel configuration as shown in FIG. 15.

The channel configuration of FIG. 15 thus essentially decouples the pressure driven flow rate up the capillary 1202 from that in the reaction channel 1216. The ratio of the overall flow rate (or velocity, assuming that the various channel segments have the same or substantially the same cross-sectional dimensions) up the capillary 1202 to the flow rate (or velocity) feeding the heated channel region 1216 is indicative of the amount of pre-concentration that will occur, assuming that all of the DNA is extracted during the selective ion extraction step. The ratio of the overall flow rate (or velocity, assuming that the various channel segments have the same or substantially the same cross-sectional dimensions) up the capillary 1202 to the flow rate (or velocity) feeding the heated channel region 1216 is preferably on the order of about two, for example about five, for example about ten or more. For example, if 3 nl/s of fluid is processed through the capillary 1202, and the total velocity ($V_T$) of the species through channel region 1208 is about 3.2 mm/s (as shown in FIG. 16C), compared to a total species velocity just prior to the heated channel region of about 0.4 mm/s, then conservation of species requires an approximate eight fold increase in DNA concentration (assuming that channel regions 1208 and 1216 have the same channel cross sectional dimensions). If channel regions 1208 and 1216 do not have the same channel cross-sectional dimensions, then the flow rates through those channel regions would need to be compared to accurately predict the concentration factor between the channel regions. FIG. 17 is an electropherogram showing an approximate seven to eight-fold stacking of DNA using a similar channel configuration as shown in FIG. 15. As noted above, samples which may be concentrated and extracted by the methods of the present invention may include those typically separated by electrophoretic techniques, including charged biomolecules such as peptides, proteins, nucleic acids, and polysaccharides, as well as charged synthetic polymers.

The teachings of the present invention can also be used to separate and isolate any two (or more) differently charged species from each other, and finds particular applicability, for example, for separation of a substrate and product from one another where the product bears a different charge from the substrate. For example, the substrate can generally include, e.g., one member of a specific binding pair, i.e., antibody/antigen pairs, receptor/ligand pairs, complementary nucleic acids or analogs thereof, binding proteins and their binding sites. Alternatively, or additionally, the substrate may comprise a substrate which is modified by the reaction of interest, e.g., by addition to, subtraction from or alteration of the chemical structure of the substrate. Some specific examples of such substrates include, e.g., kinase substrates which include phosphorylatable moieties, e.g., serine, threonine and tyrosine phosphorylation sites, and the like, phosphorylated substrates for phosphatase enzymes, amino or keto containing substrates subject to amino transferases, alcohols converted to carboxyls (e.g., via glucose-6-phosphate dehydrogenase), as well as substrates for: sulfatases; phosphorylases; esterases; hydrolases (e.g., proteases); oxidases, and the like.

The substrate may be charged, either positively or negatively, or it may be neutral, depending upon the nature of the assay that is to be performed. Preferably, the substrate will include a detectable label such that it can be detected at a detection window in the device. The fluorescent label on the substrate may be selected from any of a variety of different fluorescent labeling compounds. Generally, such fluorescent labeling materials are commercially available from, e.g., Molecular Probes (Eugene, Oreg.). Typically, fluorescein or rhodamine derivatives are particularly well suited. These fluorescent labels are coupled to the substrate, e.g., covalently through well known coupling chemistries. For a discussion of labeling groups and chemistries, see, e.g., Published International Patent Application No. WO 98/00231, which is incorporated herein by reference.

The substrate, once mixed with a reagent, generally reacts, interacts or otherwise associates or binds with the reagent to produce a fluorescent product that includes a substantially different charge than the substrate. As with the substrate, the reagent optionally comprises one member of a specific binding pair, e.g., the member that is complementary to the substrate, provided that the hybrid of the two members of the binding pair bears a charge that is different from the charge of the substrate. In many cases, this involves a reagent that is charged while the substrate is neutral, or a reagent that is highly charged as compared to a substrate that is only moderately charged. Alternatively, the association of the substrate and reagent confers a conformational change that yields a charged product, or binds to and masks charged residues on the substrate.

Another novel technique, similar to selective ion extraction described above, for separating and extracting analytes having different mobilities (e.g., different charge and/or mass) which takes advantage of the use of multiport pressure and electrical control of fluid flow, is described next with reference to FIGS. 12–14. In this embodiment of the present invention, the microfluidic channel network is configured and dimensioned to proportion the fluidic driving forces to separate differently charged species in a fluidic sample by utilizing a reduced number of external pressure and voltage sources, e.g., by reducing the number of fluidic reservoirs needed for fluidic control to perform the separation as compared to previously described embodiments. In this way, excess hardware needed for fluid transport can be minimized and the microfluidic device can be operated with fewer fluidic reservoirs compared to previously described designs.

Figure 12A:
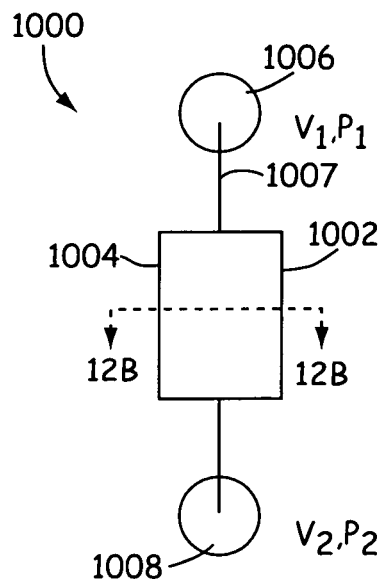
FIG. 12A is an alternative embodiment of a chip channel design for use in separating and extracting two differently charged species in a sample from one another using a form of selective ion extraction.
Figure 12B:
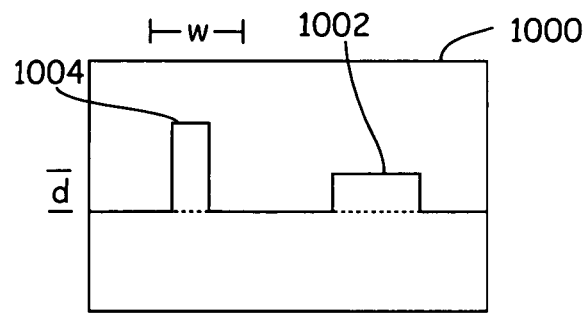
FIG. 12B is a cross-sectional view of the device of FIG. 12A taken along the line 12B—12B of FIG. 12A.

As shown first with reference to FIGS. 12A–B, a microfluidic device 1000 is configured to include a network of at least two parallel channels 1002, 1004 that are connected to two fluidic reservoirs, e.g., sample reservoir 1006 (which is fluidly coupled to sample inlet channel 1007) and waste reservoir 1008, which are in turn each operably coupled to a pressure (or vacuum) source and a voltage (or current) source (represented by the reference letters $P_1/P_2$ and $V_1/V_2$, respectively). Although only two parallel channels 1002, 1004 of equal length are shown for convenience in FIGS. 12A–B, it is to be appreciated that the microfluidic channel network can be configured with more than two channels, and with channels of varying lengths, depending on the requirements of a particular assay system and on the number of species to be separated, as will be described further below. Further, the two channels need not be in a parallel configuration as shown, but can be arranged in any configuration relative to one another, e.g., in a y-shaped configuration, in a channel "T" configuration in which channels 1002, 1004 are arranged opposed to each other, etc, in which configuration the two (or more) channels used for separation of species need not be fluidly coupled to the same waste reservoir, but may be individually coupled to their own separate reservoir or well on the chip.

By varying the ratio of the pressure driven flow to the electrokinetic flow in each channel of the parallel channel network, analytes having different electrophoretic mobilities or velocities can be separated and extracted from one another. For example, when a single pressure differential and voltage potential is applied across sample reservoirs 1006, the fluidic materials from the sample reservoir 1006 flow into the parallel channels 1002, 1004 in a ratio that is related to the flow resistances of the channels, which in turn is related to, for example, the relative depth, width and/or lengths of the respective channels. In particular, in electroosmotic fluid propulsion or direction, for a given voltage gradient, the rate of flow (volume/time) generally varies with the depth of the channel for channels having an aspect ratio of >10 (width:depth), e.g., the electrical resistance per unit length of a channel is proportional to the cross-sectional area (width times depth) of the channel. With some minor, inconsequential error for the calculation, this general ratio also holds true for lower aspect ratios, e.g., aspect ratios >5. Conversely, the hydrodynamic resistance for the same channel is inversely proportional to the third power of the channel depth (e.g., $R_h = d^{-3}$). Thus, for example, if the depth "d" of channel 1004 is doubled relative to the depth of channel 1002, the width of the channel 1004 could be halved to maintain the same electrical resistance in both channels 1002 and 1004. Thus, it is possible to construct a parallel set of channels that have identical electric fields applied to them but have variable amounts of pressure driven flow. For example, assume the width of channel 1004 is 75 microns and its depth is 10 microns, while the width of channel 1002 is 150 microns and its depth is 5 microns, as shown, for example, in FIG. 12B (which is not drawn to scale). Because the cross-sectional areas of channels 1002 and 1004 are the same (e.g., 750 microns $^2$), both channels 1002, 1004 have the same electrical resistance. However, the hydrodynamic resistance of channel 1002 is larger than channel 1004 approximately by a factor of eight (e.g., $R_{h1002}/R_{h1004}=10^3/5^3=8$). Using this type of geometry, it is possible to separate (and extract) two (or more) differently charged species from one another as described further below.

Figure 12C:
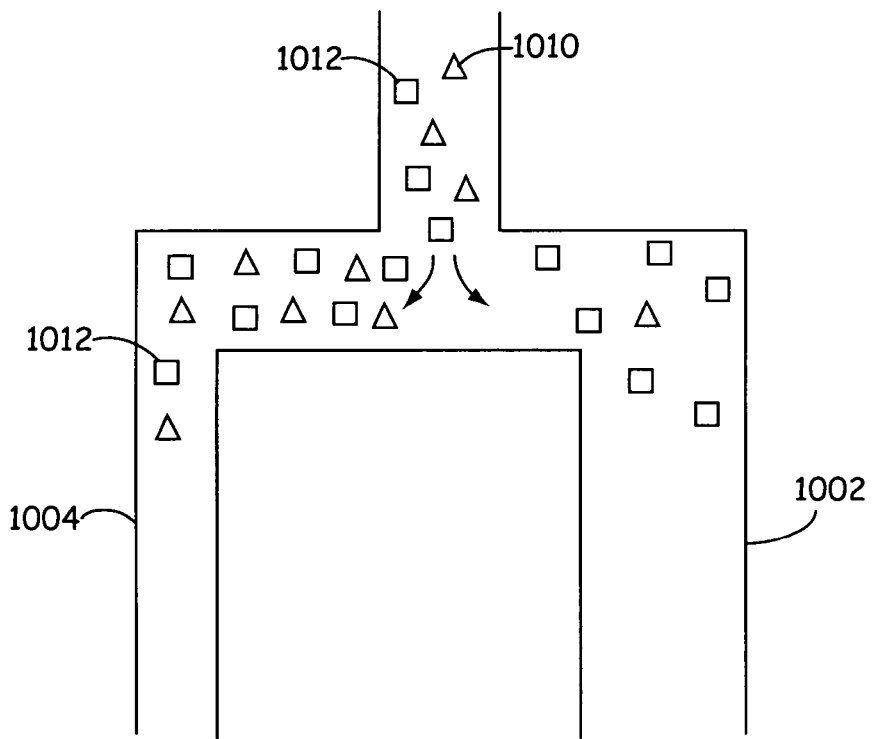
FIG. 12C is an enlarged view of the channel configuration of FIG. 12A showing separation and extraction of two differently charged species from one another.

For example, consider the case in which $P_1>P_2$ setting up a pressure driven flow from sample reservoir 1006 to waste reservoir 1008, and $V_1>V_2$ creating an electric field in channels 1002 and 1004 from reservoir 1006 towards reservoir 1008. This situation is appropriate for separating two differently charged species 1010, 1012 from each other as shown in FIG. 12C, which is an enlarged view of the parallel channel configuration of FIG. 12A. Certain assumptions are made herein, such as, for example, species 1010 is assumed to have a zero charge (e.g., $Z=0$) while species 1012 is assumed to be highly negatively charged (e.g. $Z=-2$). Although these assumptions are made herein for the purposes of simplicity and clarity, it is to be noted that the principles of this fluidic division technique may be applied for separating any one or more species from a mixture as long as the one or more species are charged (for a single species) or differently charged (for two or more species) or alternatively as long as two or more species have the same charge but have a different mass. A different charge encompasses positive versus negative charge, a high positive charge versus a lower positive charge, as well as a high negative charge versus a lower negative charge.

If the electrophoretic velocity of the negatively charged species 1012 is substantially greater than its pressure driven velocity, the charged species 1012 will be driven substantially equally into channels 1002 and 1004, because the electrophoretic velocity of the charged species 1012 substantially exceeds its pressure driven velocity and the applied electric field is identical in both of these channels. The other, neutral species 1010, on the other hand, will substantially follow the pressure-driven flow and will be substantially driven into the less hydrodynamically resistive, deeper channel 1004 (e.g., about 89% of the total amount of the neutral species will enter channel 1004 while only about 11% of the total amount will enter channel 1002) based on the ratio of hydrodynamic resistances in the channels as calculated above. Although in this simplified example the separation efficiency is not perfect, by carefully tuning the geometry and/or applied pressures and/or voltages in the system, the separation efficiency can be maximized.

The device 1000 may also include one or more side channels which are fluidly coupled to channel segments 1002 and/or 1004 if it is necessary or desirable to extract and isolate one or more of the separated species 1010 and/or 1012 for further analysis and/or detection. In addition, one or both of channel segments 1002 and 1004 may include a detection window which is in sensory communication with a detection system for detecting the separated species of interest. Detection systems may be based upon a variety of well known detection methods, including fluorescence spectroscopy (laser induced and non-laser methods), UV spectroscopy, electrochemical detection, thermal detection, capacitance based detection (see Published PCT Application No. WO 99/39190), mass spectrometry based detection, e.g., MALDI-TOF and electrospray, which can be readily configured to receive materials directly from capillary or microfluidic device outlets, and the like. In preferred aspects, optical detection methods, and particularly fluorescence based detection methods are used. Such detection systems generally include an excitation light source that provides light at an appropriate wavelength to excite the particular fluorescent species that is to be detected. The excitation light is then transmitted through an appropriate optical train, including lenses, filters (e.g., wavelength and/or spatial filters), beamsplitters, etc., and directed through, e.g., an objective lens, at a translucent portion of the separation conduit. As fluorescent species, constituents or fractions of the sample material pass through the excitation light, they fluoresce. The fluorescent emissions are then collected and transmitted back through the objective lens and the same or an alternate optical train to a light sensor, e.g., a photodiode, photomultiplier tube, CCD or the like. The device may also include one or more light altering optical elements (such as a lens or optical filter) integrated into the body structure of the device as is more fully described in U.S. Pat. No. 6,100,531 assigned to the same assignee of the present invention, the entire contents of which are incorporated by reference herein. Such devices with integrated optical elements perform at least a portion of the optical manipulations used in the optical detection scheme employed.

Figure 14A:
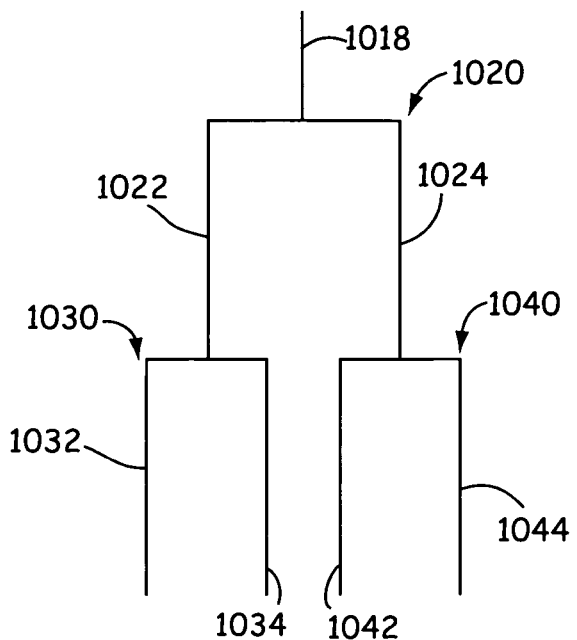
FIG. 14A is another alternative embodiment of a chip channel design for use in separating and extracting two differently charged species in a sample from one another using a form of selective ion extraction using a cascade of parallel separation channels similar to those shown in FIG. 12A.
Figure 14B:
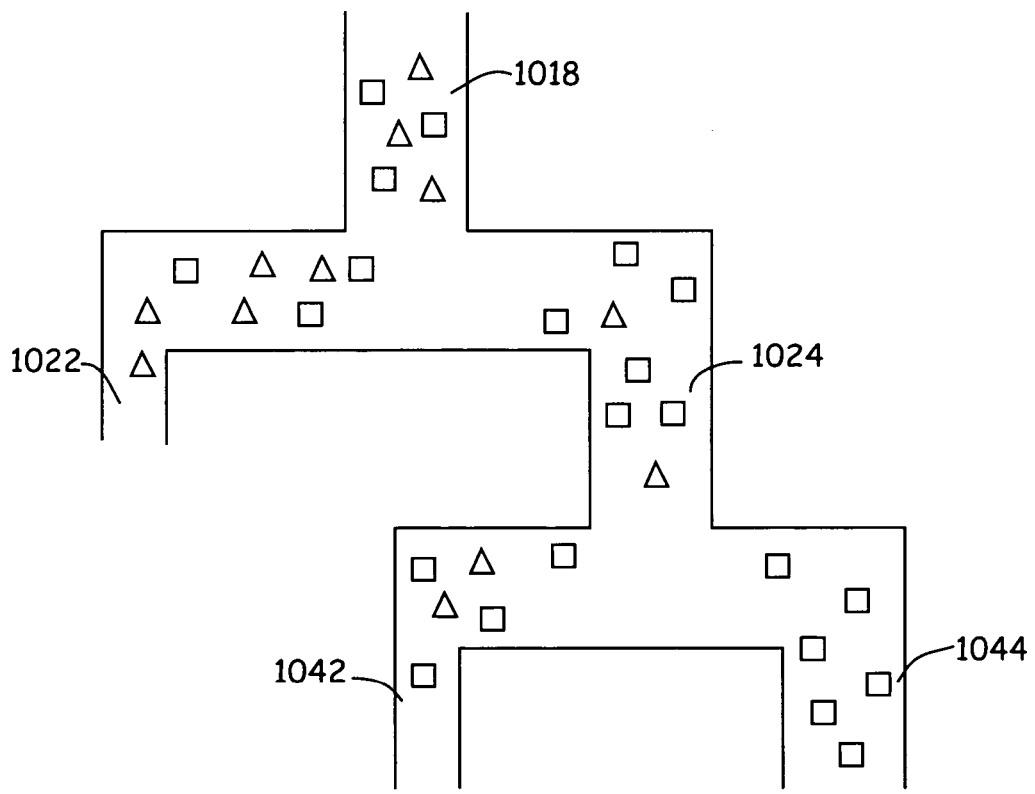
FIG. 14B is an enlarged view of a portion of the channel configuration of FIG. 14A showing the improvement in separation efficiency of the two differently charged species from one another.

The separation efficiency of the system can be enhanced by stringing together in series a plurality of parallel channel networks so that the separation can occur in a plurality of (e.g., two or more) stages, as shown, for example, in FIGS. 14A–B. As shown in FIG. 14A, the chip design can include a multiple of parallel channel networks, e.g., channel networks 1020, 1030, and 1040, which are strung together in series to form a cascade channel configuration. The hydrodynamic resistances of the channels can be chosen (e.g., their respective depths and widths (and/or lengths)) varied such that, for example, the two differently charged species can be separated from one another in multiple stages and thus with greater efficiency. This can be accomplished, for example, by designing the channel configuration such that channels 1034 and 1044 have the same or similar configuration (e.g., the same or similar hydrodynamic resistance) to channel 1024 (which, e.g., has half the depth and double the width of channel 1022, similar to FIGS. 12A–C above), while channels 1032 and 1042 have the same or similar configuration to channel 1022.

For example, consider the situation in which a sample introduced into channel 1018 of channel network 1020, contains approximately equal amounts of charged species 1012 and neutral species 1010 (e.g., about 50% of each species). Assuming again that the electrophoretic velocity of the negatively charged species 1012 is substantially greater than its pressure driven velocity, the charged species 1012 will be driven substantially equally into channels 1022 and 1024, and thus channels 1022 and 1024 will contain approximately equal amounts of charged species 1012, while channel 1024 will contain only about 11% of the total amount of the neutral species 1010 as compared to channel 1022, resulting in an approximate 8 to 1 ratio of the total amount of neutral species in channel 1022 as compared to neutral species in channel 1024. Next, after passing through the next separation stage of channel network 1040, channel 1044 will contain equal amounts of charged species 1012 as compared to channel 1042; however, the neutral species will be further separated by a ratio of 8 to 1 in channel 1042 versus channel 1044, resulting in a total amount of about 1/64 of the neutral species which was originally present in channel 1018 flowing into channel 1044. Thus, the ratio of charged species 1012 to neutral species 1010 in channel 1044 will be much greater than the ratio of charged species to neutral species in channel 1024, thus improving the separation efficiency of the system. Of course, one or more additional separation stages (e.g., parallel channel networks) can be added further downstream in the system to further improve upon the separation efficiency, if desirable or necessary for a particular application.

Generally, the depths of the channels may be varied to obtain optimal flow conditions for a desired separation of differently charged species. As such, depending upon the application, for a given parallel channel network, the first parallel channel may be greater than about two times as deep as the second channel, for example greater than about 5 times as deep as the second channel, for example greater than about ten times (or more) as deep as the second channel. However, one potential problem with using increasing depth as a variable to control the relative flow rates in the parallel branches of the channel network is that the substrate thickness and potential manufacturing constraints may limit the relative depths of the two parallel channels to a factor of 2 or 3, for example. Moreover, in the event that it is necessary to separate more than two differently charged species from one another, a channel geometry employing many different channels may be required in which the pressure driven velocity is different by a known amount from channel to channel (and the electric field is kept constant across all the channels as described above). While the number of channels may not be limited for a given substrate configuration, the number of different depths that can be used may be limited to 3 or fewer different depths for the plurality of channels due to fabrication constraints.

Figure 13A:
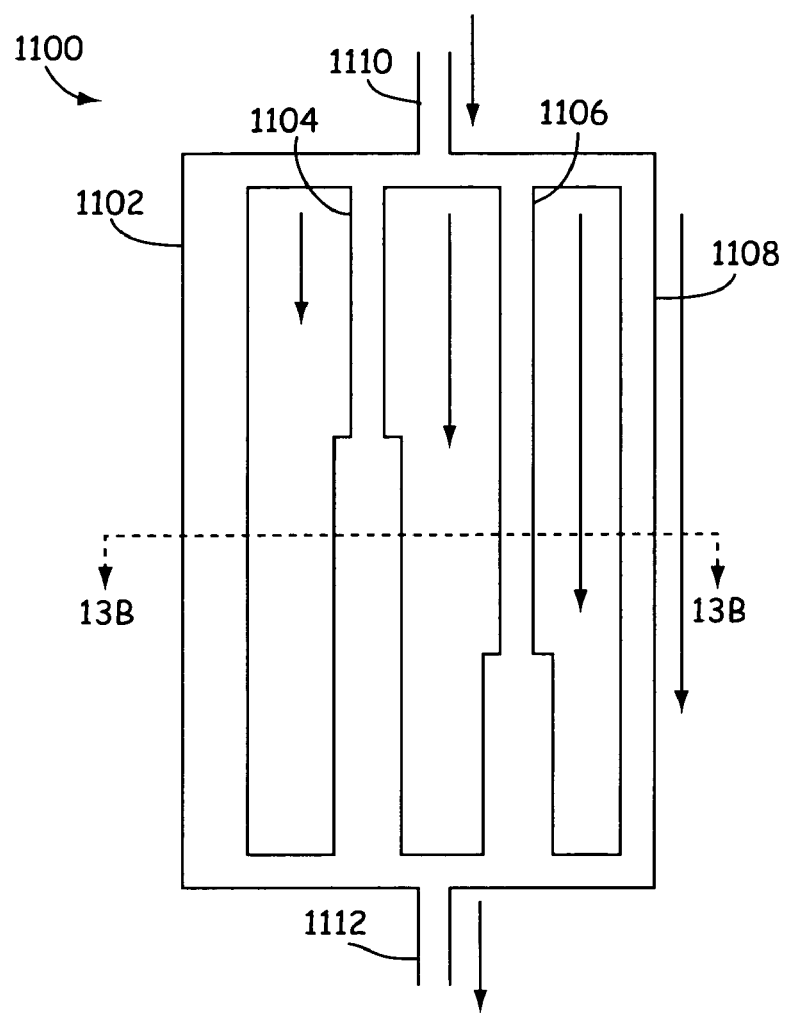
FIG. 13A is an alternative embodiment of a chip channel design for use in separating and extracting a plurality of (e.g., two or more) differently charged species in a sample from one another using a form of selective ion extraction.
Figure 13B:
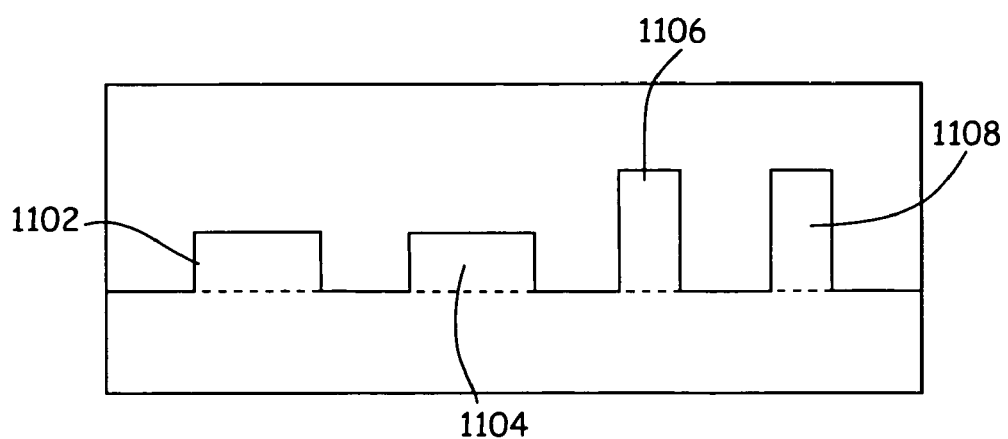
FIG. 13B is a cross-sectional view of the device of FIG. 13A taken along the line 13B—13B of FIG. 13A.

FIGS. 13A–B illustrate one possible way to separate multiple differently charged species using a combination of two different depths along the length of the channel network. As shown in FIGS. 13A–B, channel network 1100 includes four parallel channels 1102, 1104, 1106, and 1108 which are each fluidly coupled to an input channel 1110 (e.g., which is fluidly coupled to a sample reservoir (not shown)) and an output channel 1112 (e.g., which is fluidly coupled to a waste reservoir (not shown)). Although only two channel depths (and correspondingly two channel widths) are used for each of the four channels 1102–1108 as shown, for example, in FIG. 13B, the channel depths are varied along the lengths of each of the channels to create variable amounts of pressure-driven flow (e.g., by varying the hydrodynamic resistance of each channel) along the length of each channel while maintaining the same applied current potential in each respective channel (due to each channel having the same cross-sectional area along the length of the channel). The differential hydrodynamic resistances of the respective channels could also be further modified, for example, by again having the multiple channels have the same cross-sectional area, but different lengths, and therefore further varying flow resistances from one channel to another. In addition, the system can be configured to vary one or more or both of the pressure and/or voltage differential across the various channel networks of the device to achieve intended separation efficiencies. For example, the electric field can be fixed and the pressure flow varied, or the pressure flow can be fixed and the electric field varied, or both the electric field and pressure flow can be varied simultaneously to achieve the intended separation. Further, where the two or more channels in which separation of species is desired are not fluidly coupled to the same waste reservoir, the electric field need only be varied (or held fixed) across at least one of the two (or more) channels (e.g., the channel having the smaller depth and greater width) in order to achieve separation of two or more species with different electrophoretic mobilities.

c. Multistage Extraction:

In another aspect, the present invention provides methods and devices for performing multistage extractions using the selective ion extraction procedure(s) described above. Multistage extractions provide the added benefit of separating a species having a charge that is intermediate of the charge of at least two other species. For instance, while single stage selective ion extraction is suitable for separating out the species with the highest or the lowest electrophoretic mobility, multistage extractions are desirable for separating out species of intermediate mobilities as well as the species having the slowest and the fastest electrophoretic mobilities. Therefore, multistage selective ion extraction provides even more versatility in performing separation of fluid borne species contained in a mixture and thereby facilitates the use of microfluidic technology for an even wider variety of uses than what has been realized thus far.

One such use is the combination of microfluidic devices with secondary analytical instruments for the performance of specific analysis by an external device. A highly desirable combination apparatus is combining a microfluidic system with a mass spectrometer so that the separation of components of a mixture is carried out in a microfluidic device and a separated material is loaded by electrospray (or other means) into a mass spectrometer for further analysis. Such a combination and various chip to mass spectrometer interfaces are described in detail in co-owned pending application U.S. Ser. No. 60/362,291, filed Mar. 6, 2002 and U.S. Pat. No. 5,872,010, each of which is incorporated herein by reference in its entirety and for all purposes.

In the past, one of the limitations in making such a combination apparatus work has been the extremely small yield of the separated component due to the extremely small fluid volumes used in a microfluidic device. Multistage selective ion extraction as performed by the devices and systems of the present invention allows one to overcome this hurdle by performing continuous separation and isolation of a material for as long a duration as is necessary to collect enough material sufficient for the secondary analysis.

FIG. 8 illustrates a system suitable for multistage extraction. As noted above, multistage extraction is achieved by performing a series of separations using the selective ion extraction method described above. Device 800 comprises a channel network having a main channel and at least two side channels intersecting the main channel. The two side channels may intersect the main channel in any layout, e.g., formation of a four way intersection forming a cross, formation of an offset T intersection, formation of side by side T intersections, formation of an offset T etc. For simplicity, the layout shown in FIG. 8 comprises an offset T intersection. The pressure and voltage applied at each channel are configured to selectively extract a species (B) having an electrophoretic mobility ($\mu_{ep}$) that is intermediate between the electrophoretic mobilities of at least two other species (A, C) contained in a fluid plug. The device further comprises a sample source, i.e., a reservoir or an external capillary element as shown, for continuously introducing fluid plugs into the main separation channel 804. To illustrate the operation of the device, FIG. 8 shows components A, B and C flowing into main channel via a sample source. The flow of the fluid plug into channel segment 812 is driven by a negative pressure applied at reservoir 806. Therefore, the net velocity of all the species contained in the fluid plug is equal to their hydrodynamic velocity and is therefore the same in channel segment 812. When the fluid plug enters segment 814, it is subjected to an electric field created by an electric potential applied at reservoir 806. Therefore, in channel segment 814 the flow of all the species entering the segment is controlled by the hydrodynamic flow as well as electrophoretic flow. The net velocity of each of the components is a sum total of their hydrodynamic velocity and their electrophoretic velocity. The differences in the electrophoretic mobilities of the components results in a finite difference in their total velocities in segment 814 causing a separation of the various species as they flow through channel segment 814. Additionally, the electric potential applied via reservoir 806 is set at a level sufficient to counterbalance the negative pressure applied at that reservoir so as to draw component C, which has an electrophoretic mobility slower than components A and B into channel segment 824, while allowing components A and B to proceed flowing into channel segment 816. However, components A and B continue to flow with different net velocities due to their different electrophoretic mobilities. As components A and B flow into channel segment 818, they are subjected to a change in applied pressure and electric fields due to a negative pressure and an electric potential applied via reservoirs 808 and 810. The pressure and electric potential settings at reservoirs 808 and 810 are once again configured to only allow component B to flow into channel segment 822 while component A and some of component B flow into channel segment 820.

Typically, microfluidic channel networks operated in accordance with the present invention are interfaced with controller instrumentation that deliver the requisite forces to the channel segments of the network in order to establish the flow profiles described herein. While such control elements could be integrated into a self contained microfluidic device in the form of integrated pumps, valves and electrical power supplies, such devices would likely be prohibitively expensive and difficult to reliably manufacture. Instrumentation systems used in conjunction with microfluidic channel networks according to the present invention will typically include positive and/or negative pressure sources for generating pressure based flow profiles in portions of the channel network, as well as electrical power supplies for generating electrokinetic flow profiles in other segments of the network. Such systems will also typically include one or more interface components for delivering pressure energy to one or more channel segments of the network, and for delivering electrical energy to other channel segments in the network.

Figure 5:
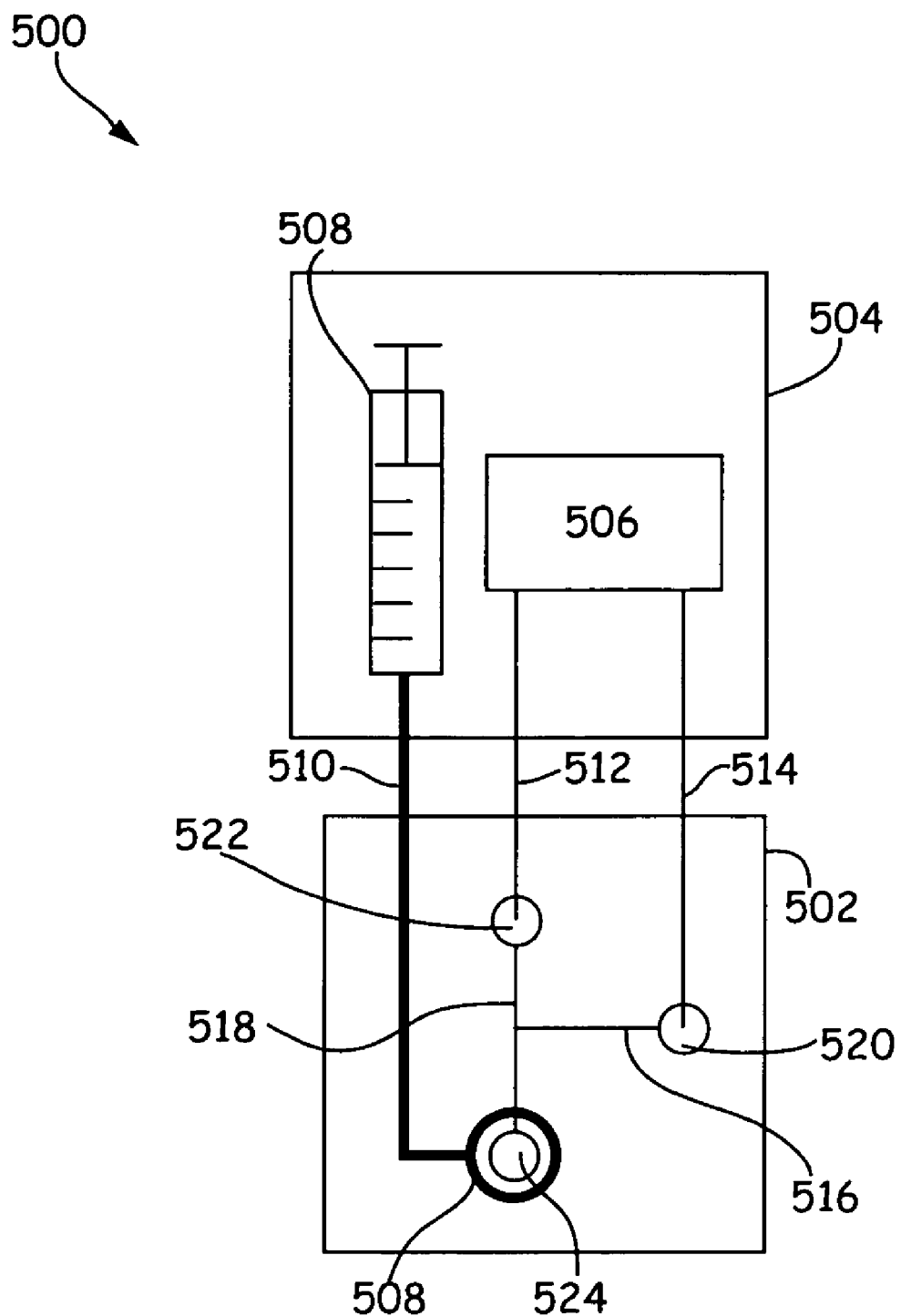
FIG. 5 is a schematic illustration of a system for carrying out the methods of the invention.

Examples of instruments that employ both pressure and voltage or current sources include the Agilent 2100 Bioanalyzer, Caliper 100 as well as the Caliper AMS 90 High Throughput Analysis system. Both systems include electrical power supplies and pressure sources (typically vacuum sources) that are interfaced with reservoirs on microfluidic devices. These reservoirs are in fluid communication with the channel networks within the devices and communicate the electrical or pressure energy to those channels. In general, such instruments could be used with a microfluidic device in order to operate in accordance with the present invention. One example of such a system 500 is schematically illustrated in FIG. 5. For ease of illustration, a simple T channel structure is shown within microfluidic device 502. Device 502 is interfaced with controller 504, and the electrical power supply 506 and pressure source 508 contained therein, through appropriate interface components. Typically, the interface components are housed in a modular interface component that contains interfaces for both pressure and electrical connection, as well as potential other interfaces, e.g., for temperature control, optical detection, position or orientation, etc.

In the case of the Agilent 2100 Bioanalyzer, interface module comprises a clam-shell that closes over the upper surface of the microfluidic device such that pressure port 510 and electrodes, e.g., electrodes 512 and 514, operatively engage the reservoirs of the device 502. Pressure port 510 is operatively connected to the pressure source 508 via a pressure line and is also sealingly mated with the appropriate reservoir of the device 502. This is accomplished by a sealable fitting, e.g., o-rings, that allows the pressure port to sealingly engage its associated reservoir. Although illustrated as a syringe pump, it will be appreciated that a variety of different pressure sources may be employed within the controller, including peristaltic pumps, or other positive displacement pumps, including, e.g., diaphragm pumps, screw pumps, and the like. IN optional aspects, additional pressure and/or vacuum sources may be provided coupled to the other reservoirs of the microfluidic device 502, in order to more precisely regulate the pressure based flow throughout the channel network in the device.

In the case of electrodes 512 and 514, a variety of interfaces are optionally employed, e.g., as described in U.S. Pat. Nos. 5,955,028 and 6,071,478, which is incorporated herein by reference in its entirety for all purposes. Typically, for simplicity of fabrication, pin electrodes are disposed on the interface module and positioned to insert into the reservoirs of the microfluidic device 502, contacting fluids disposed therein. By contacting fluids in the reservoirs, electrical currents are passed from the electrical power supply 506 in controller 504 to fluids within the channels of the device.

In the case of the Caliper AMS 90 System, the interface module is typically similar to that of the 2100 Bioanalyzer, except that the microfluidic device is placed on a hinged platform that swings up from underneath the interfacing components, rather than as a clam shell that closes over the top of the device. Typically, because the AMS 90 system is utilized for high throughput applications, the interface module is also configured to hold microfluidic devices that include an integrated capillary element, e.g., that extends from a lower surface of the device to draw a series of sample materials into the device for analysis, e.g., as schematically illustrated in FIG. 4, and as shown in FIG. 6B. As such, the interface component, and particularly the platform upon which the device is mounted includes an aperture through which the pipettor is inserted, allowing the pipettor to access sample sources outside of the interface component. Examples of both lower throughput "planar" devices and high throughput or "sipper" devices are illustrated in FIGS. 6A and 6B, respectively.

Figure 6A:
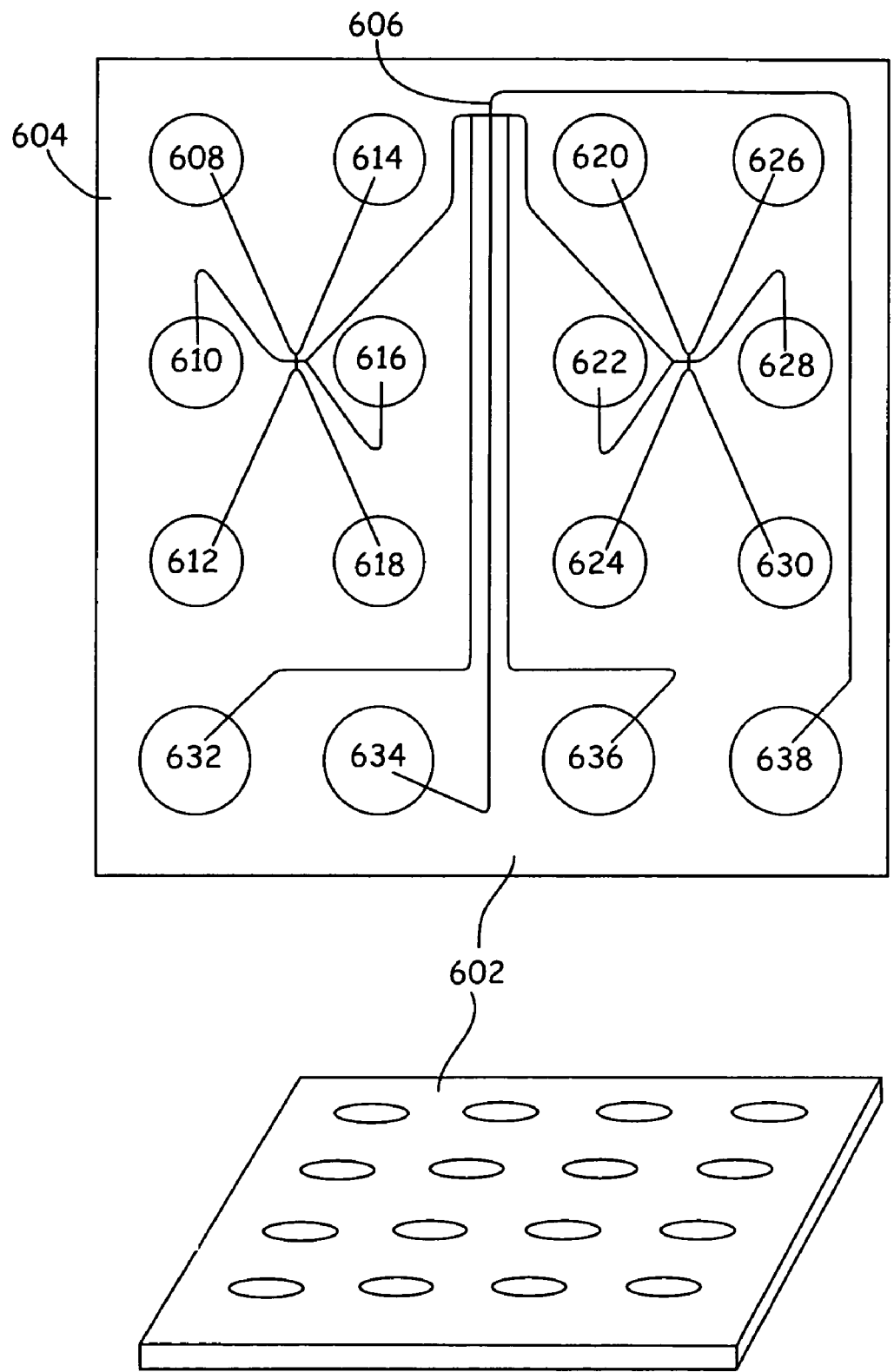
FIG. 6, panels A and B are illustrations of planar and sipper format microfluidic devices, respectively.
Figure 6B:
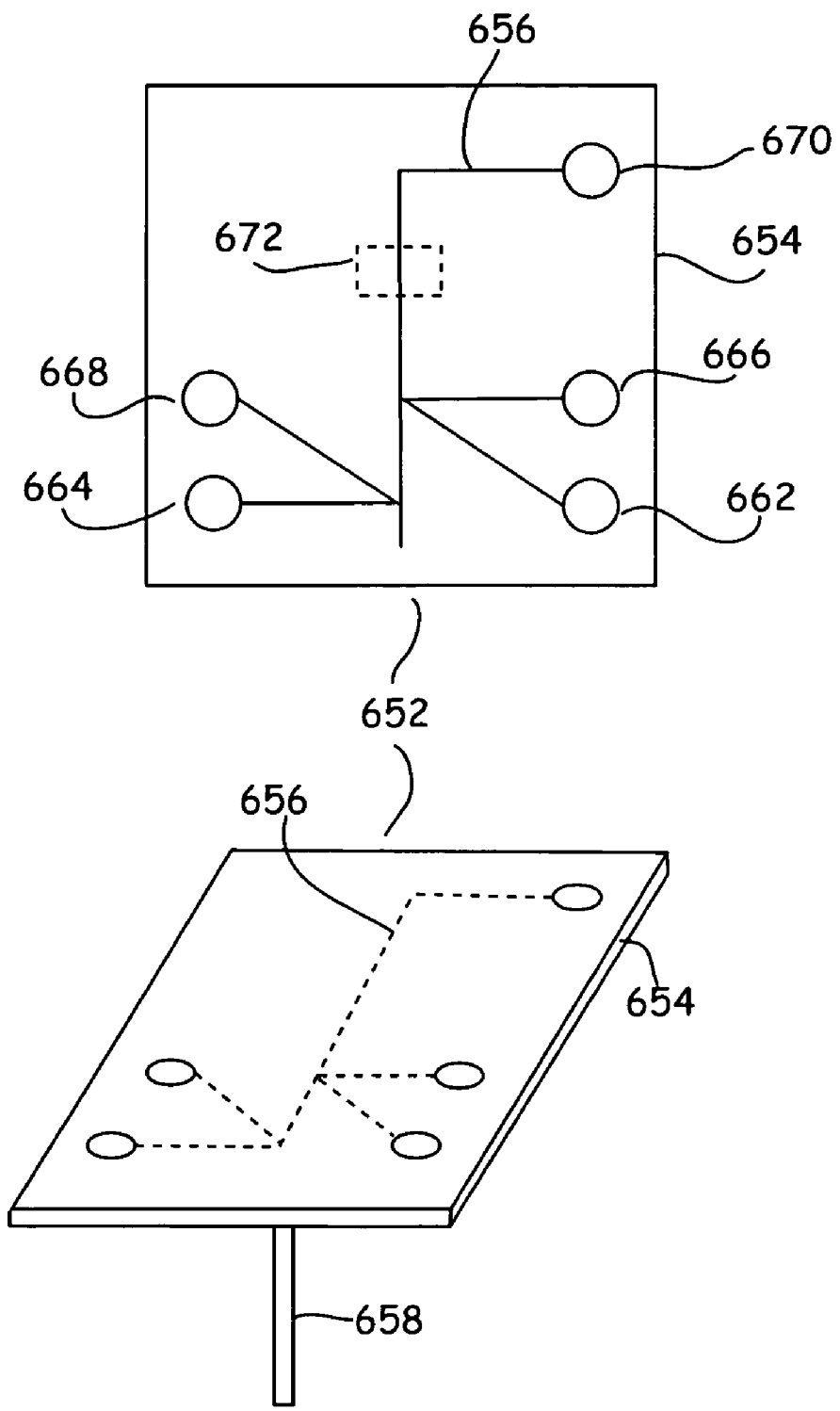

A planar device 602 is illustrated in FIG. 6A. As shown, the device 602 is similar to that shown in FIG. 6B, except that it does not include an external sampling pipettor. Samples that are to be analyzed are placed in one or more reservoirs contained within the device's overall body structure 604, e.g., reservoirs 608–630 that are in communication with channel network 656 inside the device. Reagents and buffers are typically either introduced as an admixture with the samples or they are introduced through separate reservoirs, e.g., reservoirs 632–638. Again, these reservoirs provide fluid access as well as points of access for the interface components of the controller system. In the case of the Bioanalyzer, as with the AMS 90 High Throughput system, multiple access points are provided for electrical access, while, typically only a single reservoir is used to apply a negative pressure to the channel network. In commercial applications, microfluidic devices, including both planar and sipper formats are often attached to plastic caddies that aid in handling the devices, and or provide larger volumes for the various reservoirs of the devices (see, e.g., LabChip® microfluidic devices available from Caliper Technologies Corp. and Agilent Technologies Inc.)

As shown in FIG. 6B, the high throughput devices 652 include a generally planar body structure 654 that contains a microfluidic channel network 656. A sampling capillary or pipettor 658 is attached to the body structure 654 such that the channel in the pipettor 658 is in fluid communication with the channel network 656. Materials drawn into the pipettor are moved into the channel network for further processing and/or analysis. A plurality of reservoirs, e.g., reservoirs 660 and 662 are provided at the channel termini and are in fluid communication with those channels. These reservoirs form the access points for delivering different fluids to the cannels of the device, including, e.g., reagents, buffers, dyes, etc., to mix with sample materials brought in through the pipettor element. A number of other reservoirs, e.g., reservoirs 666–670, provide access for additional reagents, e.g., diluents, etc. as well as provide access for driving pressures, electrical currents, etc. As noted above with respect to FIG. 5, such reservoirs also provide access points for the pressure and electrical interface components. Detection of reaction results is generally carried out optically, e.g., via optical detection window 672, using the detection systems described herein and generally known in the art.

Although commercially available systems can be operated with appropriate microfluidic devices in order to practice the present invention, in some cases, controller systems utilizing multiple pressure sources in addition to electrical power supplies can be used in order to establish the flow profiles described herein. In particular, by controlling the relative pressure at multiple nodes of the channel network, one can gain more precise control over the flow profiles generated in the device. With reference to FIG. 5, for example, one can more precisely regulate the pressure flow in channel segment 518 by controlling pressure applied at both ends of that channel segment, e.g., reservoirs 522 and 524, and optionally at reservoir 520 in the same fashion as shown in FIG. 5. Examples of such instrumentation include, e.g., the Caliper 42 Development Station, commercially available from Caliper Technologies Corp (Mt. View, Calif.), that is used in developing and designing microfluidic assay strategies. These systems include multiport pressure control, e.g., pressure control at multiple reservoirs of a device, as well as multiport electrical control. Multiport pressure controllers are generally described in published PCT application No. WO 01/63270, which is hereby incorporated herein by reference in its entirety for all purposes.

EXAMPLES

Example 1

Separation of a Charged Species Using a Multiport Control System and a off-Chip Assay Microfluidic Device Reagents:
  Enzyme: Protein Kinase A, a camp-dependent Protein Kinase, (Promega, Madison, Wis.)
  Substrate: 5-FAM-LRRASLG_CONH1 of molecular weight 1129.5 d
  Buffer: 5 mM MgCl2 (Sigma, St. Louis, Mo.), 0.01% Triton-X (Sigma), 1 mM DTT (Calbiochem), 10 µM ATP (Sigma), 2% DMSO (Burdick & Jackson, Muskegon, Mich.), in 100 mM HEPES buffer Apparatus:
  All experiments were performed either with a Caliper 100 development system or a Caliper 220 high-throughput screening system that were equipped with a multiport cartridge (Caliper Technologies Corp., Mountain View, Calif.). These systems are designed to provide a complete, integrated solution for primary assay screening. Each system includes automated sampling robotics, an arc-lamp or laser-based fluorescence detection system, and a complete software package for control and analysis. The chip mounts inside a cartridge, which provides the interface and alignment to the multiport pressure and voltage controller. Briefly, the multiport control module provides basic control capabilities needed for microfluidic chips. Using ambient air as the control medium, 8 independent peristaltic pumps can provide 5 psi at either positive or negative (vacuum) pressure. The voltage controller provides 8 separate high voltage lines capable of reaching ±3 KV. The multiport module is typically controlled through a script that contains the order, duration and magnitude of each function such as the pressure or voltage settings.

Figure 9:
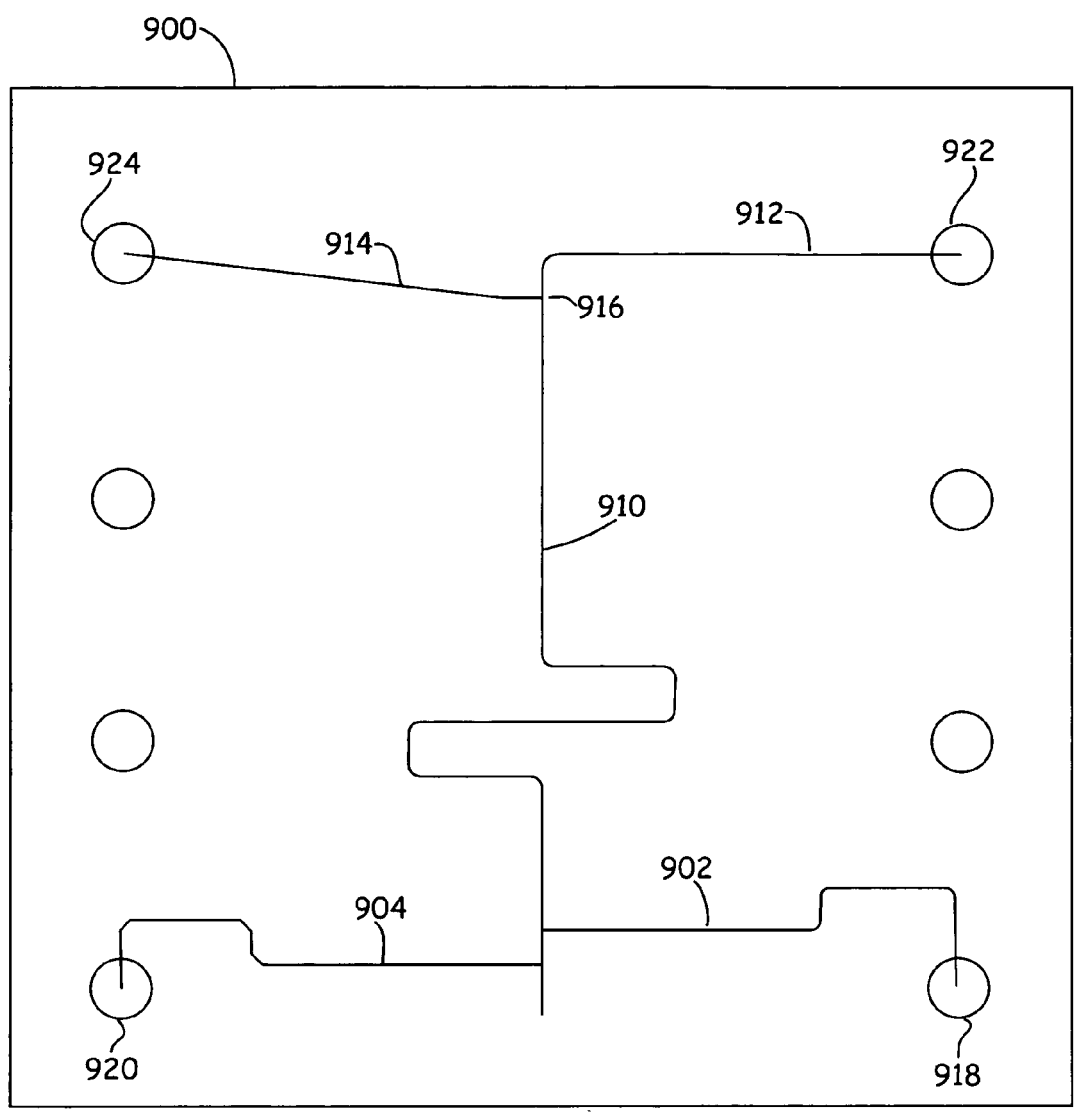
FIG. 9 illustrates a typical chip design for use in selective ion extraction based separation of charged species from a mixture.

Chip Description:
  The schematic diagram of the microchip used in this Example is shown in FIG. 9. As shown, microfluidic chip device 900 includes channel segment 902 which is fluidly coupled to enzyme reservoir 918, channel segment 904 which is fluidly coupled to substrate reservoir 920, main channel segment 910 which includes a T-intersection 916, and channel segments 912 and 914 which are fluidly coupled to respective waste (and/or analyte) reservoirs 922 and 924 respectively. Thus, sample and enzyme introduced into channel segments 902 and 904 by pressure-driven flow, electrokinetic flow, or the like, mix and interact in main channel segment 910 to produce a product reaction mixture which comprises substrate, product, and enzyme, wherein the product bears a different charge from the substrate. The reaction mixture can then be separated at T-intersection region 916 according to the methods of the present invention. The Caliper 100 and 220 analysis systems hold the device 900 such that the fluorescence detection region is located close to the end of the main channel segment 910 near to its intersection with channel segment 912. A video camera and monitor connected to the optical system allowed for visualization of the detector location on the chip. The detector was first located 0.2 mm prior to the T-intersection junction 916, using the inner corner of the T-junction as a reference point. Based on the flux model of FIG. 10, the pressures and voltages applied to the chip 900 established conditions such that no product or substrate was expected to pass the T-intersection junction. A series of peaks (FIGS. 11A–C "before" peaks) were collected at the detector, which provided the pre-junction peak characteristics. Next, the detector was repositioned 0.5 mm downstream from inner corner of the T-junction 916. Substrate and enzyme were again mixed to produce a reaction product mixture which was then detected at the detection region located downstream of the T-intersection junction 916.

Reagent Preparation:

Deionized water (18.2 MΩ-cm at 25°C.) used to prepare reagents was purified using a MilliQ® system. A 1 M HEPES buffer at pH 7.5 was prepared using ULTROL grade HEPES in both the free acid (Calbiochem, San Diego, Calif.) and sodium salt form (Calbiochem). All solutions were filtered through 0.2 μm polypropylene syringe filters before addition to the chip. Aqueous solutions of a peptide substrate and product specific for Protein Kinase A were prepared in an assay buffer at pH 7.5. Protein Kinase A (PKA), a cAMP-dependent Protein Kinase, (Promega, Madison, Wis.) was reacted with a custom synthesized substrate 5-FAM-LRRASLG-CONH2 (Caliper Technologies Corp., Mountain View, Calif.) of molecular weight 1129.5. The 5-FAM is a fluorescein NHS ester moiety (Molecular Probes, Eugene, Oreg.) attached to leucine on the amino terminus of the peptide. The custom peptide purity is equal to or greater than 98% measured by HPLC. The PKA assay buffer consists of 5 mM $MgCl_2$ (Sigma, St. Louis, Mo.), 0.01% Triton-X (Sigma), 1 mM DTT (Calbiochem), 10 μM ATP (Sigma), 2% DMSO (Burdick & Jackson, Muskegon, Mich.), in 100 mM HEPES buffer. Dynamic coating reagent 3 (Caliper Technologies Corp.) was added to the buffer to suppress electroosmotic flow. At pH 7.5, the PKA enzyme converts the neutrally charged (Z=0) substrate into a negatively charged (Z=−2) product. Aliquots of enzyme and substrate stock solutions were stored at −80° C. until needed. All solutions were stored on ice prior to reaction. In a polypropylene centrifuge tube, 100 μL of assay buffer containing 100 μM substrate and 25 nM enzyme were allowed to react to completion at room temperature for 90 minutes. The assay buffer was filtered at 0.2 μM prior to addition of the enzyme and substrate and 80 μL of 10 mM EDTA (Sigma) was added to stop the reaction. The purity of the product was checked via capillary electrophoresis, and the concentration verified via UV absorption using an extinction coefficient (ε) of 82,000 $M^{-1}cm^{-1}$ at 508 nm. Aliquots of product and substrate were stored at −80° C. until needed for individual experiments.

Figure 10:
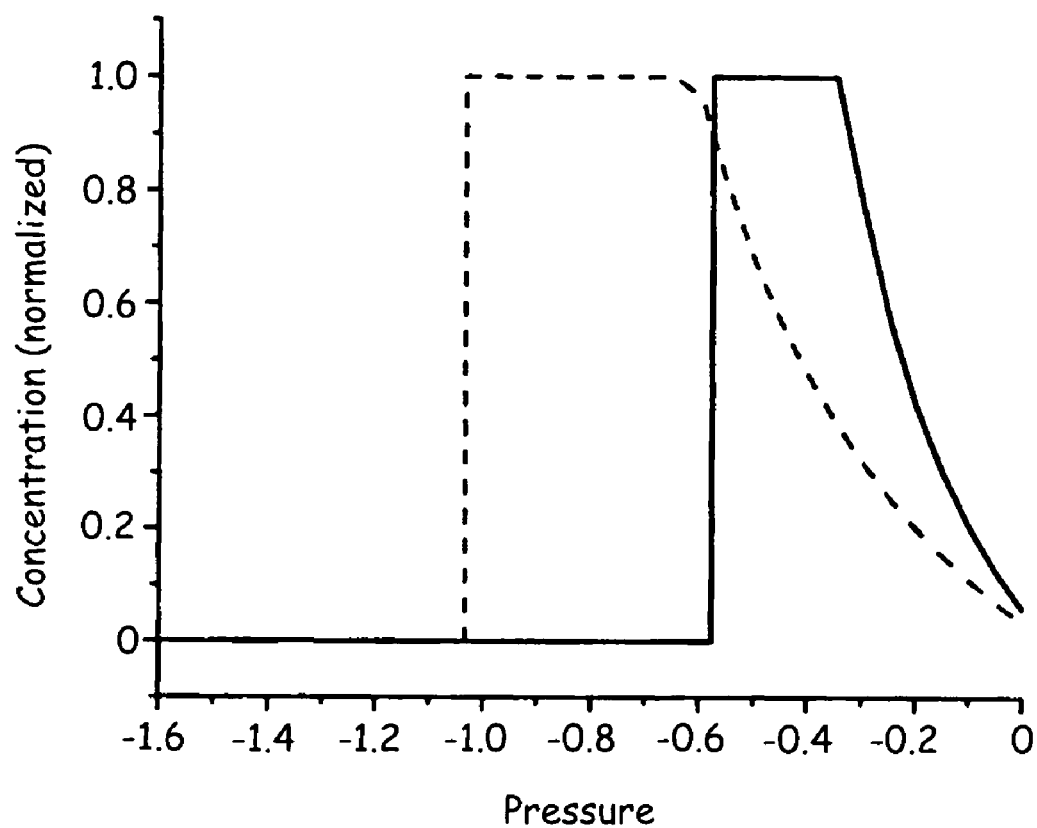
FIG. 10 illustrates a flux model of two differently charged species as a function of change in pressure.
Figure 11A:
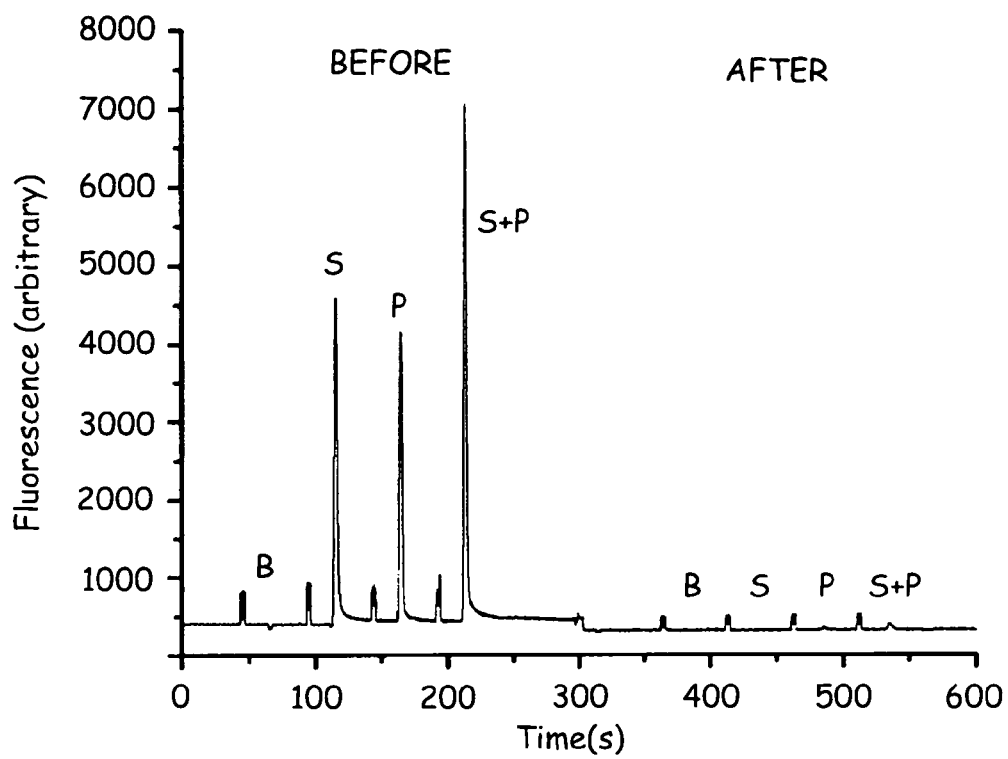
FIG. 11, panels A, B and C illustrates the fluorescence intensities of multiple charged species before and after separation at a T-junction of a device.
Figure 11B:
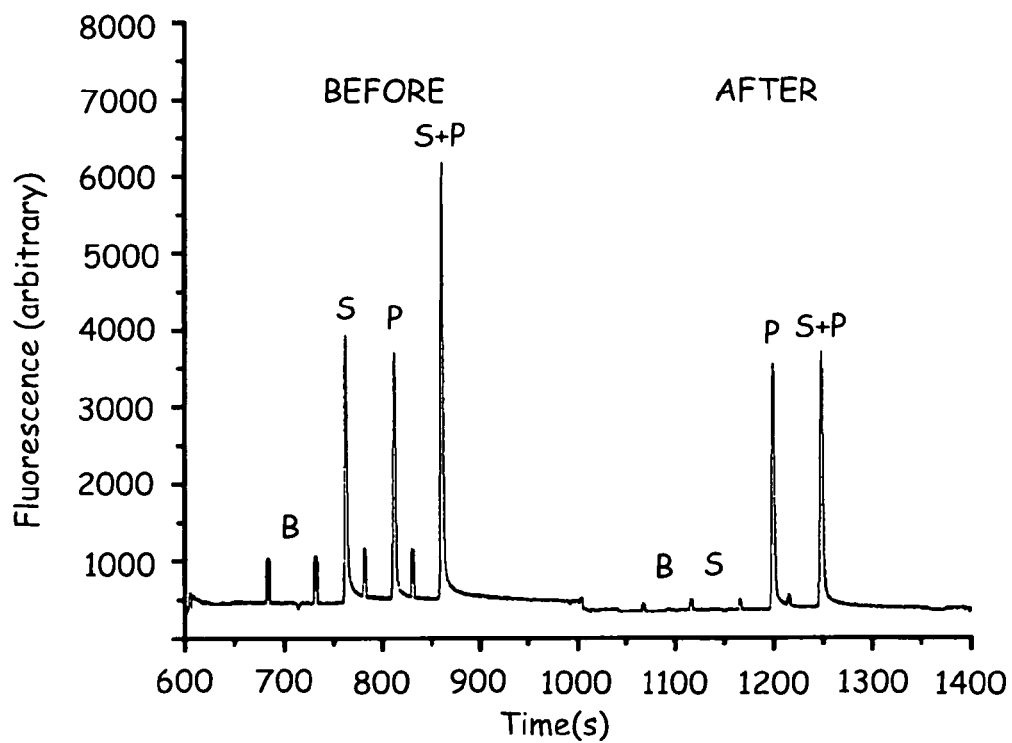
Figure 11C:
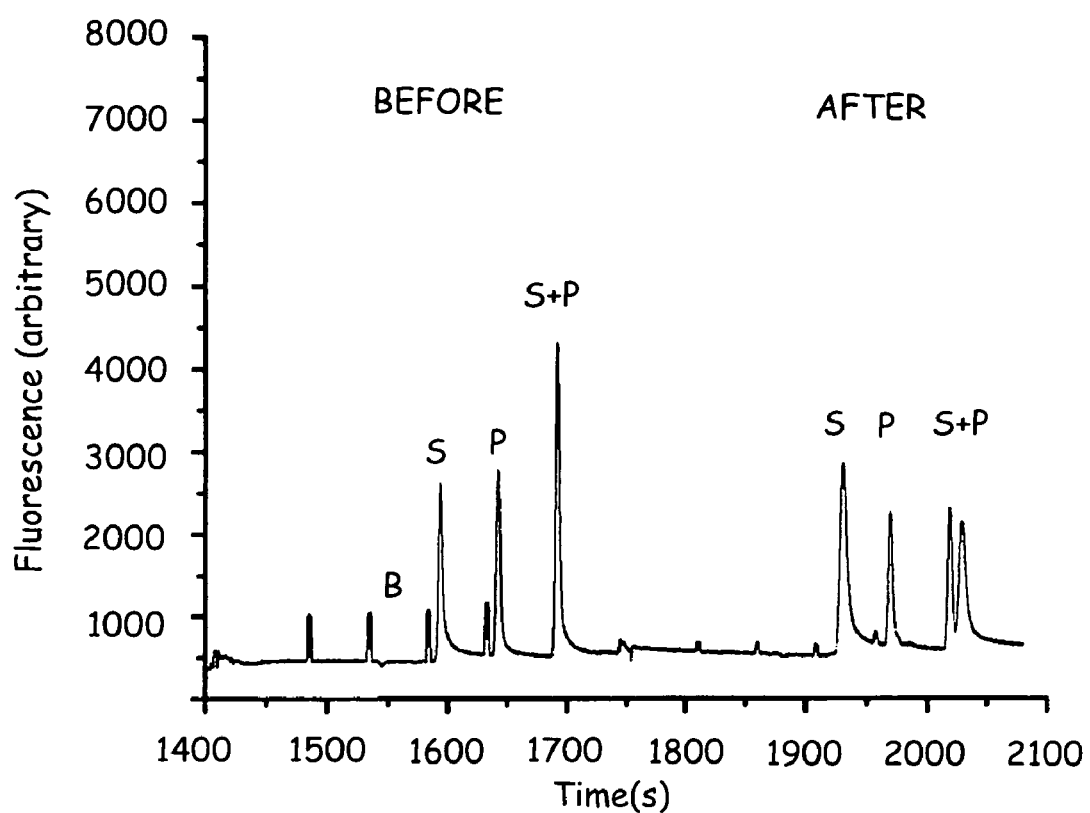

Results:

Reference is made to FIGS. 10 and 11A–C in which a simple species flux and flow velocity calculation was used to predict the actual separation of the two charged species, e.g., PKA substrate (solid line) having a neutral charge (e.g., Z=0) from the negatively charged peptide product (dotted line) (e.g., Z=−2) by the enzymatic reaction of the substrate. FIG. 10 is a predicted flux model of PKA product (dotted line) and substrate (solid line) concentration at the detector region as a function of pressure in side channel segment 914. FIGS. 11A–C summarize the results that demonstrate three regions of operation using selective ion extraction of PKA compounds recorded before and after the T-intersection separation junction, and provide fluorescence intensity peaks of PKA substrate and product recorded "before" and "after" the T-intersection 916 based on the flux model of FIG. 10. The fluorescence peaks of FIGS. 11A–C are labeled as B (background), S (substrate), P (product), and S+P (substrate and product) corresponding to buffer, substrate, product; and product and substrate, respectively. The small peaks between samples in the figure are optical noise due to the robotic movement in the prototype machine.

For a mixed sample of product and substrate flowing down the main channel segment 910, for example, a pressure of less than about −1.0 psi in channel segment 914 (e.g., by controlling the pressure gradient at reservoirs 924 and 922) will prevent both the negatively charged peptide and the neutral substrate from reaching the detector past T-intersection 916, and thus product and substrate will flow into channel segment 914. Thus, as shown in FIG. 11A, for example, at a pressure setting of −1.5 psi, there is no product or substrate detected at the detection region past the T-intersection 916. As the pressure in channel segment 914 gradually increases to a level greater than about −1.0 psi as shown in FIG. 10, only the negatively charged product is extracted into the detection channel segment 912, while the neutral substrate will continue to flow into channel segment 914. Thus, as shown in FIG. 11B, for a pressure setting of −1.0 psi in channel segment 914, only the product will be detected at the detection region past the T-intersection 916. Thus, there is a window of separation between the product and substrate with different electrophoretic mobilities as the pressure on the side channel 914 changes between about −1.0 psi and −0.6 psi. As the pressure on the side channel segment 914 increases past about −0.6 psi as shown in FIG. 10, the hydrodynamic flow reverses direction in the side arm channel segment 914, and both the substrate and product are detected past the T-intersection 916 as shown in FIG. 11C where a pressure of −0.5 psi was set in channel segment 914.

What is claimed is:

1. A method of extracting a charged species from a sample and concentrating it, comprising:

providing an interconnected channel network comprising a first, second and third channel segment which intersect at a first fluid junction, the second channel segment terminating in a first fluid reservoir at one end and intersecting the first fluid junction at its other end, and a fourth channel segment intersecting the third channel segment at a second fluid junction at one end and terminating in a second fluid reservoir at its other end, the second fluid reservoir comprising a first buffer;

flowing the charged species in the sample in a second buffer through the interconnected channel network by applying a first pressure differential across the first and second channel segments and a second pressure differential across the third and fourth channel segments, wherein the first pressure differential is larger than the second pressure differential and the first buffer has a different ionic strength than the second buffer; and applying a voltage differential across the first and second reservoirs which is sufficient to cause a substantial portion of the charged species in the sample in the first fluid junction to flow into the third channel segment.

2. The method of claim 1, wherein the first, second, third and fourth channel segments are disposed in a body structure of a microfluidic device.

3. The method of claim 1, wherein the first pressure differential is generated by applying a vacuum to the first fluid reservoir.

4. The method of claim 1, wherein the second pressure differential is generated at least in part by applying a positive pressure to the second fluid reservoir.

5. The method of claim 1, wherein the first buffer has a higher ionic strength than the second buffer.

6. The method of claim 1, wherein the difference between the first pressure differential and the second pressure differential is such that a pressure driven flow rate or velocity in the first channel segment is at least about two times greater than a pressure driven flow rate or velocity in the third channel segment.

7. The method of claim 1, wherein the difference between the first pressure differential and the second pressure differential is such that a pressure driven flow rate or velocity in the first channel segment is at least about five times greater than a pressure driven flow rate or velocity in the third channel segment.

8. The method of claim 1, wherein the difference between the first pressure differential and the second pressure differential is such that a pressure driven flow rate or velocity in the first channel segment is at least about ten times greater than a pressure driven flow rate or velocity in the third channel segment.

9. The method of claim 1, wherein the difference between the first pressure differential and the second pressure differential is such that a pressure driven flow rate or velocity in the first channel segment is at least about twenty times greater than a pressure driven flow rate or velocity in the third channel segment.

10. The method of claim 1, wherein an electrokinetic velocity of the charged species in the second channel segment is greater than its pressure driven velocity.

11. The method of claim 1, wherein an electrokinetic velocity of the charged species in the fourth channel segment is less than its pressure driven velocity.

12. The method of claim 1, further comprising a fifth channel segment fluidly coupled to the second fluid junction, wherein a total flow rate or velocity of the charged species in the fifth channel segment is about five times less than a total flow rate or velocity of the charged species in the third channel segment.

13. The method of claim 1, further comprising a fifth channel segment fluidly coupled to the second fluid junction, wherein a total flow rate or velocity of the charged species in the fifth channel segment is about ten times less than a total flow rate or velocity of the charged species in the third channel segment.

14. The method of claim 1, wherein the charged species is DNA or RNA.

15. The method of claim 14, further comprising amplifying the DNA or RNA one or more times in a fifth channel segment of the interconnected channel network.

16. The method of claim 1, wherein the first buffer forms a fluid boundary with the second buffer in the second fluid junction sufficient to concentrate the charged species in or near the second fluid junction.

17. The method of claim 16, wherein the charged species is concentrated at least about five times in or near the second fluid junction.

18. The method of claim 16, wherein the charged species is concentrated at least about ten times in or near the second fluid junction.

19. The method of claim 1, wherein a substantial portion of the sample in the second buffer other than the charged species flows into the second channel segment.

* * * * *